(12) United States Patent
Van Eijk

(10) Patent No.: US 7,846,657 B2
(45) Date of Patent: Dec. 7, 2010

(54) DETECTION OF TARGET NUCLEOTIDE SEQUENCES USING LIGATION ASSAYS WITH IMPROVED OLIGONUCLEOTIDE PROBE PAIRS

(75) Inventor: Michael Josephus Theresia Van Eijk, EJ Herpen (NL)

(73) Assignee: Keygene N.V., Wageningen (NL)

( * ) Notice: Subject to any disclaimer, the term of this patent is extended or adjusted under 35 U.S.C. 154(b) by 875 days.

(21) Appl. No.: 10/560,968

(22) PCT Filed: Jun. 16, 2004

(86) PCT No.: PCT/NL2004/000428

§ 371 (c)(1),
(2), (4) Date: Mar. 19, 2007

(87) PCT Pub. No.: WO2004/111271

PCT Pub. Date: Dec. 23, 2004

(65) Prior Publication Data

US 2007/0275375 A1    Nov. 29, 2007

(30) Foreign Application Priority Data

Jul. 23, 2004    (WO) ..................... PCT/NL03/00444

(51) Int. Cl.
*C12Q 1/68*    (2006.01)
*C12P 19/34*    (2006.01)
*C07H 21/04*    (2006.01)

(52) U.S. Cl. .......................... 435/6; 435/91.2; 435/810; 536/24.3

(58) Field of Classification Search ...................... 435/6, 435/91.2, 810; 536/24.3
See application file for complete search history.

(56) References Cited

U.S. PATENT DOCUMENTS 5,424,413 A    6/1995   Hogan
5,876,924 A *  3/1999   Zhang et al. ................... 435/5

FOREIGN PATENT DOCUMENTS

| EP | 1130113 A1 | 9/2001 |
| WO | WO 95/01456 | 1/1995 |
| WO | WO 96/15271 | 5/1996 |
| WO | WO 98/04746 | 2/1998 |

* cited by examiner

*Primary Examiner*—Gary Benzion
*Assistant Examiner*—Joyce Tung
(74) *Attorney, Agent, or Firm*—Browdy and Neimark, PLLC

(57) ABSTRACT

A pair of oligonucleotide probes comprising a first oligonucleotide probe that comprises a first clamp section that is capable of hybridising to a second clamp section of a second oligonucleotide probe and a first target section that is capable of hybridising to a first section of a target DNA sequence to be detected, a second oligonucleotide probe that comprises a second clamp section that is capable of hybridising to the first clamp section of the first oligonucleotide probe and a second target section that is capable of hybridising to a second section of the target DNA sequence to be detected.

39 Claims, 7 Drawing Sheets

Probe types:

1. Linear

2. Padlock/circularizable

3. Keylock/semi-circularizable

DETECTION OF TARGET NUCLEOTIDE SEQUENCES USING LIGATION ASSAYS WITH IMPROVED OLIGONUCLEOTIDE PROBE PAIRS

FIELD OF THE INVENTION

The present invention relates to the field of molecular biology and biotechnology. In particular the invention relates to the field of nucleic acid detection, more in particular to the design and composition of (collections) of probes that can be used for the detection of nucleic acids. The invention also relates to methods for detection of nucleic acids using the probes and compositions. The invention further provides for probes that are capable of hybridising to a target sequence of interest, primers for the amplification of ligated probes, use of these probes and primers in the identification and/or detection of nucleotide sequences that are related to a wide variety of genetic traits and genes. The invention also provides for kits of primers and/or probes suitable for use in the method according to the invention.

BACKGROUND OF THE INVENTION

There is a rapidly growing interest in the detection of specific nucleic acid sequences. This interest has not only arisen from the recently disclosed draft nucleotide sequence of the human genome and the presence therein, as well as in the genomes of many other organisms, of an abundant amount of single nucleotide polymorphisms (SNP), but also from marker technologies such as AFLP and the general recognition of the relevance of the detection of specific nucleic acid sequences as an indication of for instance genetically inheritable diseases. The detection of the various alleles of the breast cancer gene BRCA 1 to screen for susceptibility for breast cancer is just one of numerous examples. The recognition that the presence of single nucleotide substitutions (and other types of genetic polymorphisms such as small insertion/deletions; indels) in genes provide a wide variety of information has also attributed to this increased interest. It is now generally recognised that these single nucleotide substitutions are one of the main causes of a significant number of monogenically and multigenically inherited diseases, for instance in humans, or are otherwise involved in the development of complex phenotypes such as performance traits in plants and livestock species. Thus, single nucleotide substitutions are in many cases also related to or at least indicative of important traits in humans, plants and animal species.

Analysis of these single nucleotide substitutions and indels will result in a wealth of valuable information, which will have widespread implications on medicine and agriculture in the widest possible terms. It is for instance generally envisaged that these developments will result in patient-specific medication. To analyse these genetic polymorphisms, there is a growing need for adequate, reliable and fast methods that enable the handling of large numbers of samples and large numbers of (predominantly) SNPs in a high throughput fashion, without significantly compromising the quality of the data obtained. One of the principal methods used for the analysis of the nucleic acids of a known sequence is based on annealing two probes to a target sequence and, when the probes are hybridised adjacently to the target sequence, ligating the probes.

The OLA-principle (Oligonucleotide Ligation Assay) has been described, amongst others, in U.S. Pat. No. 4,988,617 (Landegren et al.). This publication discloses a method for determining the nucleic acid sequence in a region of a known nucleic acid sequence having a known possible mutation. To detect the mutation, oligonucleotides are selected to anneal to immediately adjacent segments of the sequence to be determined. One of the selected oligonucleotide probes has an end region wherein one of the end region nucleotides is complementary to either the normal or to the mutated nucleotide at the corresponding position in the known nucleic acid sequence. A ligase is provided which covalently connects the two probes when they are correctly base paired and are located immediately adjacent to each other. The presence or absence of the linked probes is an indication of the presence of the known sequence and/or mutation.

Abbot et al. in WO 96/15271 developed a method for a multiplex ligation amplification procedure comprising the hybridisation and ligation of adjacent probes. These probes are provided with an additional length segment, the sequence of which, according to Abbot et al., is unimportant. The deliberate introduction of length differences intends to facilitate the discrimination on the basis of fragment length in gel-based techniques.

WO 97/45559 (Barany et al.) describes a method for the detection of nucleic acid sequence differences by using combinations of ligase detection reactions (LDR) and polymerase chain reactions (PCR). Disclosed are methods comprising annealing allele-specific probe pairs to a target sequence and subsequent ligation with a thermostable ligase. Amplification of the ligated products with fluorescently labelled primers results in a fluorescently labelled amplified product. Detection of the products is based on separation by size or electrophoretic mobility or on an addressable array.

More in particular, one of the disadvantages of the means and methods as disclosed by Barany et al. resides in the limited multiplex capacity when discrimination is based inter alia on the length of the allele specific probe pairs. Discrimination between sequences that are distinguishable by only a relatively small length difference is, in general, not straightforward and carefully optimised conditions may be required in order to come to the desired resolving power. Discrimination between sequences that have a larger length differentiation is, in general, easier to accomplish. This may provide for an increase in the number of sequences that can be analyzed in the same sample.

Other solutions that have been suggested in the art such as the use of circular (padlock) probes in combination with isothermal amplification such as rolling circle amplification (RCA) are regarded as profitable because of the improved hybridisation characteristics of circular probes and the isothermal character of RCA. The padlock probe is generally recognised as having superior characteristics compared to the conventional linear probes (Nilsson et al. Human mutation, 2002, 19, 410415; Science 1994, 265: 2085-2088).

However, providing for the necessary longer nucleotide probes for use as padlock probes is a further hurdle to be taken. In the art, synthetic nucleotide sequences are produced by conventional chemical step-by-step oligonucleotide synthesis with a yield of about 98.5% per added nucleotide. When longer probes are synthesised (longer than ca. 60 nucleotides) the yield generally drops and the reliability and purity of the synthetically produced sequence is generally recognised as a problem.

The specific problem of providing for longer probes has been solved by Schouten et al. (WO 01/61033). WO 01/61033 discloses the preparation of longer probes for use in ligation-amplification assays. They provided probes that are considerably longer than those that can be obtained by conventional chemical synthesis methods to avoid the problem associated with the length-based discrimination of amplified products using slab-gels or capillary electrophoresis, namely that only a small part of the detection window/resolving capacity of up to 1 kilo base length is used when OLA probes are synthesised by chemical means. With an upper limit in practice of around 100-150 bases for chemically synthesised oligonucleotides according to the current state of technology, this results in amplification products that are less than 300 base pairs long at most, but often much less (see Barany et al). The difficulty of generating such long probes (more than about 150 nucleotides) with sufficient purity and yield by chemical means has been countered by Schouten et al., using a method in which the probes have been obtained by an in vivo enzymatic template directed polymerisation, for instance by the action of a DNA polymerase in a suitable cell, such as an M13 phage. This is then followed by restriction enzyme digestion by providing a short oligonucleotide sequence to create a partially double stranded sequence to create a phosphorylated 5' end of the long probe.

However, the production and purification of such 'biological probes' requires a collection of suitable host strains containing M13 phage conferring the desired length variations and the use of multiple short chemically synthesised oligonucleotides in the process, such that their use is very laborious and time-consuming, hence costly and not suitable for high-throughput assay development.

Another disadvantage of the use of circular probes is that the use of rolling circle amplification (RCA) which is commonly associated with padlock probes result in the formation of long concatamers. Examples thereof are inter alia U.S. Pat. No. 5,876,924, WO 98/04745 and WO 98/04746 by Zhang et al. who describe the ligation of circular or circularizable probes. Zhang et al. discloses the amplification of circular probes using oligonucleotide primers in RCA, using a DNA polymerase with strand displacement activity, thereby generating a long concatamer of the circular probe, starting from extension of the first primer. A second primer subsequently hybridises to the long concatamer and elongation thereof provides a second generation of concatamers and facilitates exponential amplification. Detection is generally based on the hybridisation of labelled probes. However, this method has proven to be less desirable in high throughput fashion. One of the reasons is that, for a high throughput method based on length discrimination, the use of RCA results in the formation of long concatamers. These concatamers are problematic, as they are not suitable for high throughput detection based on length based detection as this requires an additional preparation step (e.g. restriction enzyme digestion) in order to create a clearly detectable amplification product.

U.S. Pat. No. 6,221,603 disclosed a circular probe, which contains a restriction site. The probe is amplified using RCA and the resulting concatamers are restricted at the restriction site. The restriction fragments are then separated by length and detected. Separation and detection is performed on a capillary electrophoretic platform, such as the MegaBACE equipment available from Molecular Dynamics Amersham-Pharmacia. For detection (expensive) labelled dNTPs may be incorporated into the fragments during amplification, or the fragments may be detected by staining or by labelled detection probes. Digestion by the restriction enzyme is an additional step in the method for the successful detection of the target sequences and this extra step may affect the reliability of the method. Furthermore, the methods for labelling of the fragments as disclosed in U.S. Pat. No. 6,221,603 do not allow to fully utilise the capacity of simultaneous detection of multiple colours provided by most detection platforms such as the MegaBACE or others.

Accordingly, there is a need for oligonucleotide probes that combine the advantages of the various ligation probe types described herein. It is one of the goals of the present invention to provide such probes. It is another goal of the present invention to avoid the disadvantages of the commonly known probes as mentioned hereinbefore, in particular the unreliable or laborious chemical or enzymatic synthesis of relative long oligonucleotides. It is a further goal of the invention to provide for probes that are suitable for high throughput detection methods. It is also a goal of the present invention to provide for efficient, reliable and/or high throughput method for the detection of target nucleotide sequences, preferably by performing oligonucleotide ligation assays.

The present inventors have set out to eliminate or at least diminish the existing problems in the art while at the same time attempting to maintain the advantageous aspects thereof, and to further improve the technology. Other problems in the art and solutions provided thereto by the present invention will become clear throughout the description, the figures and the various embodiments and examples.

DESCRIPTION OF THE INVENTION

The present inventors have found that by a specific design of the ligation probes many of the problems outlined hereinabove can be overcome. In the present invention, for each given target sequence to be detected, preferably at least a pair of two probes is designed such that each probe in the pair is capable of hybridising to a part of the target sequence and the respective probes in the pair further each comprise a section that is complementary to the corresponding section of the other probes in the pair such that both probes are capable of hybridising to each other. The two probes in the pair are designed such that, when hybridised to each other, they are each also capable of hybridising to a target sequence. When hybridised to each other the two probes mimic or act as padlock probes when used in an oligonucleotide ligation assay for the detection of a target nucleotide sequence, whereas in the subsequent amplification and detection steps the probes can function as a linear ligation product.

DETAILED DESCRIPTION OF THE INVENTION

One of the aspects of the invention pertains to a method for the detection of a target nucleotide sequence in a sample, comprising providing at least a pair of a first and a second oligonucleotide probe for each target nucleotide sequence to be detected in the sample, whereby the first oligonucleotide probe has a section at its 5'-end that is complementary to a first part of a target sequence and the second oligonucleotide probe has a section at its 3'-end that is complementary to a second part of the target sequence, and whereby the first oligonucleotide probe further comprises a clamp section that is capable of hybridising to a complementary clamp section located in the second oligonucleotide probe whereby the clamp sections are essentially non-complementary to the target sequence, allowing the oligonucleotide probes to anneal to the target sequence, providing means for connecting the first and the second oligonucleotide probes and allowing first and second oligonucleotide probes to be connected when hybridized to adjacent sections of the target sequence to produce a connected probe corresponding to a target sequence in the sample.

One of the aspects of the invention pertains to a pair of probes (K) comprising a first probe (P1) which comprises a first target section (T1) and a first clamp section (C1), and a second probe (P2) which comprises a second target section (T2) and a second clamp section (C2), wherein the first and second clamp sections (C1, C2) are capable of hybridising to each other.

In one embodiment, the invention pertains to a pair of oligonucleotide probes (K) comprising:
- a) a first oligonucleotide probe (P1) that comprises a first clamp section (C1), that is capable of hybridising to a second clamp section (C2) of a second oligonucleotide probe (P2), and a first target section (T1) that is capable of hybridising to a first section (S1) of a target DNA sequence (D) to be detected;
- b) a second oligonucleotide probe (P2) that comprises a second clamp section (C2), that is capable of hybridising to the first clamp section (C1) of the first oligonucleotide probe (P1), and a second target section (T2) that is capable of hybridising to a second section (S2) of the target DNA sequence (D) to be detected.

When the pair of probes is brought into contact, under hybridising conditions, with a sample comprising a target sequence, the two target sections T1 and T2 of the probes will hybridise to the first S1 and second S2 sections of the target DNA sequence.

The clamp sections C1 and C2 are designed such that under the conditions under which T1 and T2 hybridise to the target DNA sequence, C1 and C2 are also hybridised to each other, forming a clamp. The configuration of the hybridised probes now resemble a padlock probe (in terms of target specific hybridisation characteristics) with a clamp.

The probes of the present invention have the advantageous hybridisation characteristics of padlock probes in terms of the favourable hybridisation kinetics, but have also the advantageous characteristics of linear hybridisation probes in terms of absence of concatamer formation during the amplification step. Hence the probes of the present invention combine the advantages of both types of probes. The probes of the present invention have a length that remains within the realms of what can be reliably synthesised using conventional chemical synthesis or other techniques, which is a significant economical advantage. A further advantage is that the probes of the present invention can be of a better quality (i.e. purity) thereby obviating additional purification of the probes, compared to (longer) padlock probes which is connected with the technical advantage that such probes are capable of significantly reducing the signal to noise ratio. Thus, the probes of the present invention combine the advantageous characteristics of circularizable/padlock probes with the advantageous synthesis and purity/quality of linear oligonucleotides of relative short length.

The method of the present invention for the detection of target sequences thus profits from the advantages of both the linear and padlock probes while avoiding the cumbersome synthesis of long oligonucleotides (padlock probes) and the unfavourable hybridisation kinetics of a pair of unlinked linear probes in the hybridisation to the target sections of the target sequence to be detected.

Probe

The pair of oligonucleotide probes are designed such that for each target sequence in a sample, a pair comprising a first (P1) and a second probe (P2) is provided, whereby the probes each contain a section (T1, T2) at one of their extreme ends that is complementary to a part of the target sequence (S1, S2). Preferably the complementary parts (S1, S2) of the target sequence are located essentially adjacent to each other. However, in certain embodiments of the invention the ends of the complementary parts (S1, S2) in the probes are not located adjacently to each other on the target sequence. Such embodiments include e.g. the embodiments described below under gap-ligation.

Within a pair of oligonucleotide probes, the first oligonucleotide probe has a section T1 at its (phosphorylated) 5'-end that is complementary to a first part S1 of a target sequence and the second oligonucleotide probe in the pair has a section T2 at its (hydroxylated)-3'-end that is complementary to a second part S2 of the target sequence. Thus, when the pair of probes is annealed to complementary parts (S1, S2) of a target sequence the 5'-end of the first oligonucleotide probe is preferably essentially adjacent to the 3'-end of the second oligonucleotide probe such that the respective ends of the two probes may be ligated to form a phosphodiester bond or another covalent bond in any suitable fashion to provide a "connected probe".

For each target sequence for which the presence or absence in a sample is to be determined, a specific pair of first and second oligonucleotide probes is designed with sections complementary to the complementary parts of each target sequence as described above. Thus, in the method of the invention, for each target sequence that is present in a sample, a corresponding (specific) connected probe may be obtained.

Thus, in the method of the invention preferably at least a pair of two oligonucleotide probes is used. However, in certain embodiments, in particular in the gap-ligation embodiments, the pair of two probes may be complemented with a third or further oligonucleotide probe. In such instances the third or further oligonucleotide probes preferably comprise, or more preferably consist of a nucleotide sequence that is complementary to a third or further part of the target sequence to be detected, such that upon successful hybridisation to the target sequence, together with the first and second oligonucleotide probes, the first, second, third and further probes may be connected or ligated to form a connected probe (see below).

Preferably, a group of multiple pairs comprising first and second oligonucleotide probes are provided, wherein each pair is complementary to a specific target sequence and the group as a whole is complementary to the multiplicity of target sequences in the sample. A pair of first and second oligonucleotide probes for a given target sequence in a sample will at least differ in nucleotide sequence from probe pairs for other target sequences, and will preferably also differ in length from probe pairs for other target sequence, more preferably a probe pair for a given target sequence will produce a connected probe and/or amplified connected probe (amplicons, obtained after optional amplification of the connected probes) that differs in length from connected probes corresponding to other targets in the sample as described below. Alternatively, connected probes and/or amplicons corresponding to different targets may have an identical length if they can be otherwise distinguished e.g. by different labels as described below. Alternatively, connected probes and/or amplicons may be distinguished based on sequence or mass rather than length, using hybridisation based methods with (labelled) probes or arrays or mass spectrometry, respectively.

The target sections in the probes of the present invention each comprise, independently, from about 15 to 35, preferably from 18 to 32, more preferably from 20 to 30 nucleotides.

In a preferred embodiment, the target section contains at least one allele-specific nucleotide, preferably at the 3' end of a target section adjacent to the phosphorylated 5' end of the second probe. The presence of an allele specific nucleotide in the probe allows for the detection of a specific SNP allele of a locus. When the complementary allele specific nucleotide is present in the target sequence S, the two probes will form a matched duplex that can be ligated to form a connected probe. Detection of the connected probe is an indication of the presence of that specific allele in the sample. In one embodiment, the sample may be provided with one or more groups of pairs of probes, preferably two or more, more preferably three or more groups of probes. By combining each of the groups with a primer that is capable of selectively amplifying only one group from amongst the other groups, a further increase in throughput can be obtained as one ligation assay can be used for the detection of different groups of target sequences.

Clamp

The clamp section is preferably located at or near the end of the probe that is distal to the target section, i.e. when the target section is located at the 3' end, the clamp section is located more towards the 5' end and vice versa. The clamp section is not necessarily located most distal at the 5' end or 3' end, it may be followed by other sections discussed herein below. The clamp sections are preferably designed such that they are not capable of hybridising to the target sections. The clamp sections of the first and second probe of the pair are capable of hybridising to each other. The clamp sections are preferably designed such that two complementary clamp sections have a higher binding affinity for each other than the binding affinity of the target section of the probe for its complementary part in the target nucleotide sequence. This means in practice that the clamp sections, when hybridised to each other, form a stronger duplex than the hybrid between the target section and its complement in the target nucleotide sequence and/or hybridization of complementary clamps takes place at higher temperatures than hybridisation of the target complementary section of the probes to the target. In other words, the hybridised clamp section denatures, under otherwise comparable conditions, at a higher temperature or higher stringency conditions than the denaturation temperature of the target complementary sections in the pair of probes. This allows to choose the conditions during the method of the invention such that the hybridised or locked clamp remains hybridised or closed at least until the probes are connected to produce a connected probe. The locked clamp can be opened by denaturing the (connected) probe at a temperature or under circumstances that allow the denaturation of the locked clamp.

A pair of probes having locked clamps express similar or identical hybridisation kinetics and behaviour as do circular or padlock probes. The two probes of a pair can be added separately after which the clamp sections are hybridised to each other in the sample or, alternatively the two probes can be locked prior to being added to the sample.

In a preferred embodiment the clamp has a denaturation temperature (or melting temperature, Tm) that exceeds the denaturation temperature of the target complementary sections in the pair of probes by at least 1° C., preferably 5° C. more preferably 10° C. compared to the lowest Tm of the T1 or T2 section. The denaturation temperature of a oligonucleotide sequence can calculated/estimated from the nucleotide composition using the general formula's for Tm=(4*G or C)+(2*A or T) or Tm=(4*G/C)+2*A/T)−5° C. (Meinkoth et al. Anal. Biochem. (1984) 138: 267-284). Other formulas are likewise applicable as the essence lies in the difference in denaturation temperature between the sections (Tm[clamp]-Tm[target]). This can be achieved not only by varying the length of the clamp sections but also by varying the GC content of the clamp, as a GC basepair increases Tm by about 2° C. compared to an AT basepair. A typical clamp section comprises 10 to 30, preferably 15 to 25 and more preferably 18 to 24 nucleotides. When the GC content is lower, this number of nucleotides may increase as long as the desired hybridisation characteristics are obtained. Alternatively modified nucleotides can be used that increase the hybridisation between the two clamp sections. Examples thereof are nucleotides that have improved hybridisation characteristics, such as Locked Nucleic Acids such as disclosed in WO 99/14226, WO 00/56748, WO 00/66604 and WO 01/25478, Peptide Nucleic Acids or by other molecules that stabilise or enhance DNA hybridisation such as minor groove binders and others, such as those in described in EP 0 974 672.

The GC content of the clamp may vary, wherein the GC content of clamp section ranges from more than 50 to 100%, preferably more than 60%, more preferably more than 70%, most preferably more than 80% and is preferably in the range of 90-100%. Hence most clamp sections will contain A/T combinations on a more incidental or structural basis. A preferred group of clamp sections are GC enriched ZIP sequences (Iannone et aL (2000), Cytometry 39: pp. 131-140). Preferably the clamp section comprises at least one, preferably at least 2, 3, 4, or 5 nucleotides selected from the group consisting of G's and C's, more than each of T1 and T2.

In a preferred embodiment, when groups of pairs are involved, a different clamp section may be provided for each pair of probes in the group. The clamp section is designed such that a clamp for a first pair of probes and clamps for a second or further pair of probes are distinguishable from each other and preferably do not cross hybridise to each other under conditions used in the ligation assay. Each pair of probes comprises a unique clamp, thereby avoiding cross hybridisation between clamps of different pairs of probes in a sample. To this end the clamp section may comprise additional nucleotides or the oligonucleotide sequences of the clamp section can be unique within the group. The use of unique clamp sections for each pair of probes in a group enables the detection of multiple target sequences in one sample simultaneously. This embodiment also enables the detection of one or more different target sequences in multiple samples subsequently, using the same collection of pairs of probes. This embodiment further enables that the same group of pairs of probes can be used over and over again for the detection of different target sequences.

Preferably, when using different clamps in a group of pairs of probes, these clamps have a Tm that is within a small range, preferably between about 60-90° C., more preferably between 65-88° C., most preferably between 70-85° C. As is known the hybridisation characteristics of nucleic acids are also influenced by the salt concentrations. As used herein, comparison of hybridisation characteristics in general or denaturation temperatures in particular of oligonucleotides is considered under comparable salt concentrations, unless indicated otherwise.

Alternative clamps that can be used in the present invention are nucleic acids that contain photodegradable links. After ligation, the photodegradable link can be removed and the connected probe amplified and/or detected.

Stuffers

The oligonucleotide probes of the present invention may further comprise a stuffer sequence (R1, R2) of a variable length. Each probe in the pair may contain a stuffer. The length of the stuffer varies from 0 to 1000, preferably from 0 to 500, more preferably from 1 to 100 and most preferred from 1 to 50. The stuffer may be a unique sequence as is known as a Zip-code sequence as described by Iannone et al. (2000), Cytometry 39: pp. 131-140. The stuffer may be located between the target section and the clamp or may be incorporated in the clamp or at the distal end from the target section. The stuffer may be used to impart length differences between probes or connected probes but can also be used to impart mass differences for mass-based detection or addressable sequences (ZIPs) for hybridisation based detection.

In a further embodiment the invention relates to a set of at least three oligonucleotides suitable for SNP genotyping, comprising:
 a) a first oligonucleotide probe (P1) that comprises a first clamp section (C1) that is capable of hybridising to a second clamp section (C2) of a second oligonucleotide probe (P2) and a first target section (T1) that is capable of hybridising to a first section (S1) of a target DNA sequence (D) to be detected;
 b) a second oligonucleotide probe (P2) that comprises a second clamp section (C2) that is capable of hybridising to the first clamp section (C1) of the first oligonucleotide probe (P1) and a second target section (T2) that is capable of hybridising to a second section (S2) of the target DNA sequence (D) to be detected;
 c) at least a third oligonucleotide probe (P3) that comprises the second clamp section (C2) that is capable of hybridising to the first clamp section (C1) of the first oligonucleotide probe (P1) and the second target section (T2) that is capable of hybridising to the second section (S2) of the target DNA sequence (D) to be detected;

wherein the second probe and the third probe contain an allele-specific nucleotide, preferably located at the end of a target section of the set of probes;

wherein the allele-specific nucleotide of the second and the third probes corresponds to the alleles of the SNP to be detected;

wherein the second and the third probes contain a further (stuffer) section that discriminates between the (amplified) ligation products of the first probe with the second probe and the third probe.

Primer Binding Sites

To facilitate amplification of connected probe pairs, primer binding sites (B1, B2) may be incorporated in the probes. Primer binding sites are preferably located in other parts of the probe than the target section, preferably between the clamp sections and the target sections. Primer binding sites are capable of binding primers to initiate primer elongation or amplification. Preferably within a group of pairs of probes, the primer binding sites are universal, i.e. only a predetermined group of primer binding sites are incorporated in the probe to enable multiplex primer elongation or amplification from a limited number of primers, such as primers comprising one or more selective bases at their 3' end, such as are known from AFLP (EP 0 534 858).

The functions of stuffer, primer binding sites and clamp section in a probe can be combined and can be interrelated in the sense that a specific part of the probe may function as (part of) a clamp section during hybridisation and ligation, at the same or another time may function as (part of) a primer binding site for primer elongation/amplification and at again the same or another time function as a stuffer to impart the desired and detection platform-based difference such as disclosed herein below.

Target Sequences

In its widest definition, the target sequence may be any nucleotide sequence of interest. The target sequence can be any sequence of which its determination/detection is desired, for instance because it is indicative, associated or representative of a certain ailment or genetic make up or disorder. The target sequence preferably is a nucleotide sequence that contains, represents or is associated with a polymorphism. The term polymorphism herein refers to the occurrence of two or more genetically determined alternative sequences or alleles in a population. A polymorphic marker or site is the locus at which sequence divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele. Other polymorphisms include (small) deletions or insertions of several nucleotides, referred to as indels. A preferred target sequence is a target sequence that is associated with an AFLP® marker, i.e. a polymorphism that is detectable with AFLP®.

DNA

In the nucleic acid sample, the nucleic acids comprising the target may be any nucleic acid of interest. Even though the nucleic acids in the sample will usually be in the form of DNA, the nucleotide sequence information contained in the sample may be from any source of nucleic acids, including e.g. RNA, polyA$^+$ RNA, cDNA, genomic DNA, organellar DNA such as mitochondrial or chloroplast DNA, synthetic nucleic acids, DNA libraries, clone banks or any selection or combinations thereof. The DNA in the nucleic acid sample may be double stranded, single stranded, and double stranded DNA denatured into single stranded DNA. Denaturation of double stranded sequences yields two single stranded fragments, one or both of which can be analysed by probes specific for the respective strands. Preferred nucleic acid samples comprise target sequences on cDNA, genomic DNA, restriction fragments, adapter-ligated restriction fragments, amplified adapter-ligated restriction fragments. AFLP fragments or fragments obtained in an AFLP-template preamplification.

Samples

It is preferred that a sample contains two or more different target sequences, i.e. two or more refers to the identity rather than the quantity of the target sequences in the sample. In particular, the sample comprises at least two different target sequences, in particular at least 10, preferably at least 25, more preferably at least 50, more in particular at least 100, preferably at least 250, more preferably at least 500 and most preferably at least 1000 additional target sequences. In practice, the number of target sequences in a sample that can be analysed is limited, among others, by the number of connected probes than can be detected. E.g., too many different pairs of first and second oligonucleotide probes in a sample may corrupt the reliability of a multiplex amplification step.

A further limitation is formed e.g. by the number of fragments in a sample that can be resolved by the detection platform used. The number can also be limited by the genome size of the organism or the transcriptome complexity of a particular cell type from which the DNA or cDNA sample, respectively, is derived.

Ligation Assay

The method of the present invention comprises the hybridisation of the pair of probes to the target sequence and the ligation of the two of probes when annealed adjacent to each other on the target sequence.

In one embodiment of the method of the present invention, the hybridisation/ligation step is performed directly on the target sequence or on a representation thereof. The resulting connected probes are then detected, preferably after being amplified. The method preferably is a method for determining the presence or absence of one or more target sequences in a nucleic acid sample. The method preferably comprises the steps of:
  a) providing to a nucleic acid sample a pair of a first and a second oligonucleotide probe for each target sequence to be detected in the sample, whereby the first oligonucleotide probe has a section at its 5'-end that is complementary to a first part of a target sequence and the second oligonucleotide probe has a section at its 3'-end that is complementary to a second part of the target sequence, whereby the first and second part of the target sequence are preferably located adjacent to each other, and wherein the first oligonucleotide probe further comprises a clamp section that is capable of hybridising to a complementary clamp section located in the second oligonucleotide probe, wherein the clamp sections are essentially non-complementary to the target sequence;
  b) allowing the clamps to anneal;
  c) allowing the oligonucleotide probes to hybridise to the corresponding parts of target sequences whereby the target complementary sections of the first and second oligonucleotide probes are preferably located adjacent;
  d) providing means for connecting the first and the second oligonucleotide probes hybridised to the target sequence;
  e) allowing the complementary sections of the annealed first and second oligonucleotide probes to be connected, to produce a connected probe corresponding to a target sequence in the sample; and,
  f) detecting the connected probes, whereby optionally the connected probes are amplified prior to detection to produce an amplified sample comprising amplified connected probes (amplicons).

In a preferred embodiment of the present invention, the clamp section is annealed (closed or locked) during the hybridisation/ligation step (i.e., steps (b) and (c) are combined in one step). In a preferred embodiment the pair of probes can be added to the sample in the form of two separate probes that under the starting conditions of the method will anneal with their respective clamp sections of the corresponding probe within the pair. In another embodiment the two probes in the pair are annealed with their clamp sections before being added to the sample. When the two clamp sections in a pair of probes are annealed, prior to or during the hybridisation/ligation step (c), the two probes act as a single circular probe with the advantageous hybridisation and ligation characteristics associated commonly associated with padlocks, i.e. increased hybridisation kinetics ascribed to the intertwining of the circular probe with the target sequence and concomitant increase in stability, thereby enhancing the chance of successful and correct ligation and reducing the number of unsuccessful events or false-positives. After hybridisation of the probes to the target sequence and ligation, the ligated or connected probes are preferably subjected to a denaturation treatment. This may open the clamp. The connected probe can be amplified using one or more primers to provide amplified connected probes in order to facilitate detection.

When the clamp section is not denatured but remains closed during the amplification step, the connected probe can still be regarded as a linear molecule, but with hybridised ends. Amplification and even exponential amplification is still possible, provided that there is a position were the amplification primer(s) can anneal. Preferably the primer binding sites provided in the probes are different from the clamp section to allow the primer(s) to anneal.

In one embodiment of the method of the invention, the hybridisation/ligation step can also be performed on an amplification product of the target sequence. The relevant section from the target sequence is then (pre-)amplified after which the probe pair is added and the ligation step is performed. In this embodiment, the label is usually provided in the probe. The probes of the present invention then have the advantage of improved hybridisation characteristics compared to conventional linear probes. An example of such amplification-ligation assay is present in WO 97/45559 (primary PCR/Secondary PCR/Ligation detection reaction).

Hybridisation

In the hybridisation step (c) of the method, one or a multiplicity of different target sequences, i.e. at least two different target sequences, is brought into contact with one or a multiplicity of specific oligonucleotide probe pairs under hybridising conditions. The pairs of oligonucleotide probes are subsequently allowed to anneal to the, preferably adjacent, complementary parts of the multiple target sequences in the sample. Methods and conditions for specific annealing of oligonucleotide probes to complementary target sequences are well known in the art (see e.g. in Sambrook and Russel (2001) "Molecular Cloning: A Laboratory Manual ($3^{rd}$ edition), Cold Spring Harbor Laboratory, Cold Spring Harbor Laboratory Press).

Usually, after mixing of the oligonucleotide probes and target sequences the nucleic acids are denatured by incubation (generally at between 94° C. and 96° C.) for a short period of time (e.g. 30 seconds to 5 minutes) in a salt buffer. The sample containing the denatured probes and target sequences is then allowed to cool to an optimal hybridisation temperature for specific annealing of the probes and target sequences, which usually is about 5° C. below the melting temperature of the hybrid between the complementary section (target section) of the probe and its complementary sequence (in the target sequence). In order to prevent aspecific or inefficient hybridisation of one of the two probes in a primer pair, or in a sample with multiple target sequences, it is preferred that, within one sample, the sections of the probes that are complementary to the target sequences are of a similar, preferably identical melting temperatures between the different target sequences present in the sample. Thus, the complementary sections of the first and second probes preferably differ less than 20, 15, 10, 5, or 2° C. in melting temperature. This is facilitated by using complementary sections of the first and second probes with a similar length and similar G/C content, the complementary sections preferably differ less than 20, 15, 10, 5, or 2 nucleotides in length and their G/C contents differ by less than 30, 20, 15, 10, or 5%. Complementary as used herein means that a first nucleotide sequence is capable of specifically hybridising to second nucleotide sequence under normal stringency conditions. A nucleotide sequence that is considered complementary to another nucleotide sequence may contain a minor amount, i.e. preferably less than 20, 15, 10, 5 or 2%, of mismatches. Alternatively, it may be necessary to compensate for mismatches e.g. by incorporation of so-called universal nucleotides, such as for instance described in EP-A 974 672, incorporated herein by reference or with LNAs or PNAs. Since annealing of probes to target sequences is concentration dependent, annealing is preferably performed in a small volume, i.e. less than 25 µl, preferably less than 10 µl. Under these hybridisation conditions, annealing of probes to target sequences usually is fast and does not need to proceed for more than 5, 10 or 15 minutes, although longer annealing time may be used as long as the hybridisation temperature is maintained to avoid aspecific annealing. Longer annealing times are more important/required for quantitative applications which rely on complete target occupation by ligation probes in order to allow monitoring of relative amounts of target sequences between samples In a preferred embodiment of the invention, excellent results have been obtained by prolonged hybridisation times such as overnight hybridisation or longer, such as 10 times 1 hour). Prolonged hybridisation times can be advantageous in these assays as the difference in signal due to different hybridisation efficiencies is reduced and it is considered desirable to achieve complete hybridisation and ligation of all probes for which a target sequence is present. Excellent results have been obtained by a combined hybridisation-ligation step using a thermostable ligase described herein. In this embodiment the hybridisation-ligation was performed by allowing the probes to hybridise during 1 hour in the presence of a thermostable ligase, followed by a denaturation step. Repeating these steps for at least 2 times provided good results. Repeating these steps 10 times provided excellent results.

To avoid evaporation during denaturation and annealing, the walls and lids of the reaction chambers (i.e. tubes or microtitre wells) may also be heated to the same temperature as the reaction mixture which is commonly achieved by the use of commercial DNA amplification equipment. In preferred oligonucleotide probes the length of the target-complementary section is preferably at least 15, 18 or 20 nucleotides and preferably not more than 30, 40, or 50 nucleotides and the probes preferably have a melting temperature from the target section of at least 50° C., 55° C. or 60° C.

Non-Hybridised Probes

The probes that are not complementary to a part of the target sequence or that contain too many mismatches will not or only to a reduced extent hybridise to the target sequence when the sample is subjected to hybridisation conditions. Accordingly, ligation is less likely to occur. The number of spurious ligation products from these probes in general will therefore not be sufficient and much smaller than the bona fide ligation products such that they are outcompeted during subsequent multiplex amplification. Consequently, they will not be detected or only to a minor extent.

A preferred method of the invention further comprises a step for the removal of oligonucleotide probes that are not annealed to target sequences and/or that are not-connected/ligated. Removal of such probes preferably is carried out prior to amplification, and preferably by digestion with exonucleases.

By removal/elimination of the oligonucleotide probes that are not connected/ligated a significant reduction of ligation independent (incorrect) target amplification can be achieved, resulting in an increased signal-to-noise ratio. One solution to eliminate one or more of the not-connected/ligated components without removing the information content of the connected probes is to use exonuclease to digest not-connected/ligated oligonucleotide probes. By blocking the end that is not ligated, for example the 3' end of the downstream oligonucleotide probe, one probe can be made substantially resistant to digestion, while the other is sensitive. Only the presence of full length ligation product sequence will then prevent digestion of the connected probe. Blocking groups include use of a thiophosphate group and/or use of 2-O-methyl ribose sugar groups in the backbone. Exonucleases include ExoI (3'-5'), Exo III (3'-5'), and Exo IV (both 5'-3' and 3!-5'), the later requiring blocking on both sides. One convenient way to block both probes is by using one long "padlock" probe (see M. Nilsson et. al., "Padlock Probes: Circularising Oligonucleotides for Localised DNA Detection," Science 265: 2085-88 (1994), which is hereby incorporated by reference), although this is by no means required.

An advantage of using exonucleases, for example a combination of Exo I (single strand specific) and Exo III (double strand specific), is the ability to destroy both the target DNA and one of the oligonucleotide probes, while leaving the ligation product sequences substantially undigested. By using an exonuclease treatment prior to amplification, either one or both (unligated) oligonucleotide probes in each set are substantially reduced, and thus hybridisation of the remaining oligonucleotide probes to the original target DNA (which is also substantially reduced by exonuclease treatment) and formation of aberrant ligation products which may serve as a suitable substrate for PCR amplification by the oligonucleotide primer set is substantially reduced.

Ligation

The respective 5'-phosphorylated and 3'-hydroxylated ends of a pair of first and second oligonucleotide probes that are annealed essentially adjacent to the complementary parts of a target sequence are connected in step (c) to form a covalent bond by any suitable means known in the art. The ends of the probes may be enzymatically connected into a phosphodiester bond by a ligase, preferably a DNA ligase. DNA ligases are enzymes capable of catalysing the formation of a phosphodiester bond between (the ends of) two polynucleotide strands bound at adjacent sites on a complementary strand. DNA ligases usually require ATP (EC 6.5.1.1) or NAD (EC 6.5.1.2) as a cofactor to seal nicks in double stranded DNA. Suitable DNA ligase for use in the present invention are T4 DNA ligase, *E. coli* DNA ligase or preferably a thermostable ligase like e.g. *Thermus aquaticus* (Taq) ligase, *Thermus thermophilus* DNA ligase, or *Pyrococcus* DNA ligase. Alternatively, chemical autoligation of modified polynucleotide ends may be used to ligate two oligonucleotide probes annealed at adjacent sites on the complementary parts of a target sequence (Xu and Kool, 1999, Nucleic Acid Res. 27: 875-881).

Both chemical and enzymatic ligation occur much more efficient on perfectly matched probe-target sequence complexes compared to complexes in which one or both of the probes form a mismatch with the target sequence at, or close to the ligation site (Wu and Wallace, 1989, Gene 76: 245-254; Xu and Kool, supra). In order to increase the ligation specificity, i.e. the relative ligation efficiencies of perfectly matched oligonucleotides compared to mismatched oligonucleotides, the ligation is preferably performed at elevated temperatures. Thus, in a preferred embodiment of the invention, a DNA ligase is employed that remains active at 50-65° C. for prolonged times, but which is easily inactivated at higher temperatures, e.g. used in the denaturation step during a PCR, usually 90-100° C. One such DNA ligase is a NAD requiring DNA ligase from a Gram-positive bacterium (strain MRCH 065) as known from WO 01/61033. This ligase is referred to as "Ligase 65" and is commercially available from MRC Holland, Amsterdam.

Gap Ligation

In an alternative embodiment, for instance directed to the identification of indels, the respective ends of the complementary sections of the first and second probe may be annealed such that a gap is left. This gap can be filled with a suitable (third) oligonucleotide and ligated. Such methods are known in the art as 'gap ligation' and are disclosed inter alia in WO 00/77260. Another possibility to fill this gap is by extension of one end of the probe using a polymerase and a ligase in combination with single nucleotides, optionally preselected from A, T, C, or G, or di-, tri- or other small oligonucleotides. In case the target sequence is RNA, yet another possibility to fill the gap is by extension of one end of the probe using reverse transcriptase and a ligase in combination with single nucleotides, optionally preselected from A, T, C, or G, or di-, tri- or other small oligonucleotides.

Cleavase Ligation

In one aspect of the present invention, an additional discriminating step can be introduced prior to ligation. In certain embodiments, the first or the second oligonucleotide probe of the pair is designed such that one of the two probes is extended beyond the foreseen point of ligation of its target-specific section. Preferably the probe is extended with a sequence that is not complementary to the target sequence. In the event of correct annealing of target-specific sections of the two probes to the target sequence, a forked cleavage structure is formed wherein the 3'-end of the target-specific section of the non-extended probe is annealed to the target sequence, while the extended 5' end of the other probe, which is non-complementary to the target sequence, forms a single-stranded arm (see FIG. 4). The thus-obtained forked cleavage structure is a substrate for the 5' nuclease activity of DNA polymerases, referred to herein as a cleaving agent, or cleavase. A preferred cleavase is a modified DNA polymerase having 5' nuclease activity but lacking synthetic activity or a FEN endonuclease. An example of such a forked cleavage structure and such a cleavase is described in EP 601834 and U.S. Pat. No. 5,795,763 (Third Wave Technologies). An example of a FEN nuclease is the multifunctional, structure-specific metallonuclease FEN-1 (five' exonuclease-1 or flap endonuclease-1), which also acts as an endonuclease for 5' DNA flaps (Reviewed in Hosfield et al., 1998, Cell, 95:135).

In certain embodiments the cleavase may be a native DNA polymerase but preferably the cleavase is a modified form that lacks the synthetic activity of the DNA polymerase. Suitable DNA polymerases with 5' nuclease activity and that may be modified to inactivate their synthetic activity are polymerases from e.g. *Thermus thermophilus, Thermus aquaticus, Escherichia coli,* and *Thermus flavus,* or a modified form of the gene 6 product from bacteriophage T7 or FEN endonuclease. Other suitable cleavases are mentioned inter alia in U.S. Pat. Nos. 6,635,463, 6,562,611, 6,555,357, 6,458,535, 6,348,314, 6,090,606, 6,090,543, 6,001,567, 5,994,069, 5,985,557, 5,843,669, 5,846,717, 5,837,450, 5,614,402, WO94/29482, WO97/27214, WO98/23774, WO98/42873.

Upon incubation of the forked cleavage structure with a suitable cleavase, cleavage will occur in the extended probe, right between the first unmatched nucleotide of the extension sequence and the first matched nucleotide of the target-specific section of the extended probe. The extension sequence is thus removed and the two ends of the target-specific sections of the first and second probes of the pair will anneal immediately adjacent to each other, in case of a perfect match with the target sequence, thus allowing for ligation of the two probes to form a connected probe (see FIG. 4). This principle is valid for and can be applied to any conventional OLA assay and the assays of the present invention alike and may form an inventive improvement of the OLA-technology by further improving the fidelity of the OLA-technology. The principle is valid for non-circularizable, circularizable and semi-circularizable probes (as described herein) alike.

In certain embodiments, the general method for the OLA-assays comprises a step wherein a cleavage structure is formed comprising the target nucleic acid sequence, a first probe and a second probe. In certain embodiments, the first probe comprises a first target specific region that is capable of annealing to a first section of the target nucleic acid sequence to form a first duplex. In certain embodiments, the second probe comprises a second target specific region that is capable of annealing to a second section of the target nucleic acid sequence to form a second duplex. In certain embodiments, the first and second sections of the target nucleic acid sequence are contiguous so that the first and the second duplexes are contiguous. In certain embodiments, the first probe or the second probe comprises a further region (E), an extended region, preferably an extended 5'-end, that is not capable of annealing to the target nucleic acid sequence. In certain embodiments, the further (extended) region is located at the end of the first or second probe at the position of the junction site (i.e. the potential site of ligation of the OLA-assay) between the first and second sections of the target nucleic acid sequence. In certain embodiments, the further (extended) region provides a non annealed section of the first or the second probe to thereby create a (forked) cleavage structure. Certain embodiments comprise exposing the cleavage structure to a cleavage agent that preferably cleaves the cleavage structure in a manner independent of the sequence of the cleavage structure results in cleavage of the cleavage structure when the cleavage structure and cleavage agent are incubated under conditions wherein cleavage can occur. In certain embodiments, cleaving the cleavage structure results in removal of the further (extended) region. In certain embodiments, the removal of the further (extended) region by cleaving the cleavage structure results in adjacent localization of the first and second probe.

In one aspect, the invention relates to the use of a cleavage agent, preferably prior to ligation, in OLA-assays. In certain embodiments, the cleavage agent is used to remove an overhang (i.e. the further or extended region) of the first or second probe located at the envisaged point of ligation such that the first and second probe can be ligated. The characteristics of the cleaving agent are that cleavage occurs when the two probes are annealed adjacent to each other on the target sequence and one of the probes has an overhang at the point where the probes are annealed adjacent. In certain embodiments, cleavage occurs preferably only when the two probes are annealed adjacent to each other on the target sequence and one of the probes has an overhang at the point where the probes are annealed adjacent. The cleavage of the overhang provides two probes that are annealed adjacent on the target sequence and that can be ligated. One of the technical advantages of this cleavage step is that the cleavage step provides the 5' phosphate at the end of one of the probes necessary for ligation. The provision of the 5' phosphate can be used as an alternative for conventional oligonucleotide synthesis wherein phosphorylation at the 5' end is one of the final steps in the synthesis of oligonucleotides. A further technical advantage is that the selectivity and specificity of the subsequent ligation reaction is significantly increased due to the improved selectivity of the cleavage agent to cleave only cleavage structures, i.e. those structures where the nucleotide in the overhang is complementary or capable of hybridizing to the nucleotide in the target sequence.

In certain embodiments directed to the allele specific detection of SNPs in target sequences, the allele specific nucleotide is incorporated in the probe that contains the further (extended) region. Thus, one probe of the pair comprises target specific section that anneals essentially adjacent to the SNP to be investigated. The other probe of the pair comprises a target specific section that contains the nucleotide that is complementary to the SNP to be investigated and, adjacent to that nucleotide, the further (extended) region. A generalized representation of this embodiment, applicable to all OLA-assay's and the present invention alike involves the use of a further (extended) region is in FIGS. 6A, 6B and 7. This embodiment allows both the cleavage step and the ligation step to occur only in case both target sections are a perfect match at the point of ligation/cleavage and this embodiment further improves specificity.

The introduction of the cleavage step in the OLA assay combines the specificity of the monoplex Invader Assay (Third Wave Technologies) with the flexible multiplex capacity of OLA SNPWave assays. This allows for instance to measure SNP frequencies in pooled or complex samples or other forms of quantitative measurement of sequences such as non-routine transcript profiling, or quantitative measurement of contamination levels of pathogens in soil, food, waters etc.

The use of this additional step in OLA assays provides significant advantages and finds application in, for instance, in the field of quantitative analysis of allele frequencies in, for instance, population screenings or in the field of identification of low-frequent mutants in complex samples.

Primers

The connected probes are amplified using at least one, preferably a pair of primers corresponding to the primer-binding sites. In a preferred embodiment at least one of the primers or the same pair of primers is used for the amplification of two or more different connected probes in a sample, preferably for the amplification of all connected probes in a sample. Such a primer is sometimes referred to as a universal primer as these primers are capable of priming the amplification of all probes containing the corresponding universal primer binding site and consequently of all ligated probes containing the universal primer binding site. The different primers that are used in the amplification are preferably essentially equal in annealing and priming efficiency. Thus, the primers in a sample preferably differ less than 20, 15, 10, 5, or 2° C. in melting temperature. This can be achieved as outlined above for the complementary section of the oligo-nucleotide probes. Unlike the sequence of the complementary sections, the sequence of the primers is not dictated by the target sequence. Primer sequences may therefore conveniently be designed by assembling the sequence from tetramers of nucleotides wherein each tetramer contains one A, T, C and G or by other ways that ensure that the G/C content and melting temperature of the primers are identical or very similar. The length of the primers (and corresponding primer-binding sites in the tags of the probes) is preferably at least 12, 15 or 17 nucleotides and preferably not more than 25, 30, 40 nucleotides.

In a preferred embodiment, at least two of the oligonucleotide probes that are complementary to at least two different target sequences in a sample comprise a primer-binding site that is complementary to a single primer sequence. Thus, preferably at least one of the first and second primer in a primer pair is used for the amplification of connected probes corresponding to at least two different target sequences in a sample, more preferably for the amplification of connected probes corresponding to all target sequences in a sample. Preferably only a single first primer is used and in some embodiments only a single first and a single second primer is used for amplification of all connected probes. Using universal primers for amplification of multiple different fragments usually is advantageous for the efficiency of the amplification step.

The connected probes obtained from the ligation of the adjacently annealed probe sections are amplified in step (d), using a primer pair, preferably consisting of a pair of primers for each of the connected probes in the sample. The primer pair comprises primers that are complementary to primer-binding sequences that are present in the connected probes. A primer pair usually comprises a first and at least a second primer, but may consist of only a single primer that primes in both directions. Excellent results have been obtained using primers that are known in the art as AFLP—primers such as described inter alia in EP 0 534 858 and in Vos et al., Nucleic Acid Research, 1995, vol. 23: 4407-44014.

Labels

In a preferred embodiment, at least one of the primers complementary to the primer-binding sites of the first and second oligonucleotide probes in the sample comprises a label, preferably the second primer comprises a label. The label can be selected from a large group, amongst others comprising fluorescent and/or phosphorescent moieties such as dyes, chromophores, or enzymes, antigens, heavy metals, magnetic probes, phosphorescent moieties, radioactive labels, chemiluminescent moieties or electrochemical detecting moieties. Preferably the label is a fluorescent or phosphorescent dye, more preferably selected from the group of FAM, HEX, TET, JOE, NED, and (ET-)ROX. Dyes such as FITC, Cy2, Texas Red, TAMRA, Alexa fluor 488™, Bodipy™ FL, Rhodamine 123, R6G, Bodipy 530, Alexafluor™532 and IRDyes™ by Licor as used on the NEN Glober $IR^2$ platform are also suitable for use in the present invention. Preferably the label may be chosen from amongst the fluorescent or phosphorescent dyes in the group consisting of FAM, TET, JOE, NED, HEX, (ET-)ROX, FITC, Cy2, Texas Red, TAMRA, Alexa fluor 488™, Bodipy™ FL, Rhodamine 123, R6G, Bodipy 530, Alexafluor™532 and IRDyes™.

By using a primer pair comprising differently labelled primers, the number of connected probes that can be discriminated in a sample and hence the number of target sequences in a sample can be doubled for each additional label. Thus, for each additional label that is used in a sample, the number of target sequences that can be analysed in a sample is doubled. The maximum number of labels that can be used in one sample in a high throughput method is governed mostly by the limitations in the detection capabilities of the available detection platforms. At present, one of the most frequently used platforms (MegaBACE, by Molecular Dynamics—Amersham-Biosciences Ltd.) allows the simultaneous detection of up to four fluorescent dyes, being FAM, JOE or HEX, NED and (ET-)ROX. However, alternative capillary electrophoresis instruments are also suitable, which includes ABI310, ABI3100, ABI3700 (Perkin-Elmer Corp.), CEQ2000 XL (Beckman Coulter) and others. Non-limiting examples of slab-gel based electrophoresis devices include ABI377 (Perkin Elmer Corp.) and the global $IR^2$ automated DNA sequencing system, available from LI-COR, Lincoln, Nebr., USA.

Amplification

Any amplification of the connected probes can be achieved successfully either with a locked clamp, or preferably, with an opened clamp, i.e. the connected probe is in the form of a linear molecule, as opposed to the circular form of the connected probe with the locked clamp. Any subsequent amplification of the connected probes of the invention can be achieved using simple and well-known amplification technologies such as PCR. One of the advantages of using conventional techniques such as PCR is that the resulting amplification product does not consists of a linear arrangement of multiple units (concatamers) as opposed to amplified concatenated linear representations, which typically result from amplification of padlock probes.

In the amplification step of the method of the invention, the connected probes are amplified to produce a (detectable) amplicon by any suitable nucleic acid amplification method known in the art. Nucleic acid amplification methods usually employ one or two primers, dNTPs, and a (DNA) polymerase. A preferred method for amplification is PCR. "PCR" or "Polymerase Chain Reaction" is a rapid procedure for in vitro enzymatic amplification of a specific DNA segment. The DNA to be amplified is denatured by heating the sample. In the present invention, this denaturation step is preferably such that the clamp section of the connected probes also denatures. In the presence of DNA polymerase and excess deoxynucleotide triphosphates, oligonucleotides that hybridise specifically to the target sequence prime new DNA synthesis. One round of synthesis results in new strands of determinate length, which, like the parental strands, can hybridise to the primers upon denaturation and annealing. The second cycle of denaturation, annealing and synthesis produces two single-stranded products that together compose a discrete double-stranded product, exactly the length between the primer ends and preferably devoid of the clamp section. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., Current Protocols in Molecular Biology, John Wiley & Sons, Inc. (1995). Suitable conditions for the application of PCR in the method of the invention are described in EP-A 0 534 858 and Vos et al. (1995; Nucleic Acids Res. 23: 4407-4414), where multiple DNA fragments between 70 and 700 nucleotides and containing identical primer-binding sequences are amplified with near equal efficiency using one primer pair. Other multiplex and/or isothermal amplification methods that may be applied include e.g. LCR, self-sustained sequence replication (3SR), Q-β-replicase mediated RNA amplification, rolling circle amplification (RCA) or strand displacement amplification (SDA). In some instances this may require replacing the primer-binding sites in the non-target complementary sections of the probes by a suitable (RNA) polymerase-binding site.

Amplicons

The term 'amplicon' as used herein refers to the product of the amplification step of the connected or ligated probes. The term amplicon as used herein thus refers to an amplified connected probe. After the ligation step wherein the two target specific sections are connected by means of a ligase, the connected or ligated probe can be combined with one or more primers and a polymerase and amplified. The ligated probe, the primers, the polymerase and/or other parameters and variables are such that the amplification results in amplified linear representations of the connected probe, as opposed to amplified concatenated linear representations, which typically result from amplification of padlock probes. In the present invention the amplicon is a linear oligonucleotide having a length that preferably does not substantially exceed the length of the connected probe. The minimum length of the amplicon is at least the sum of the length of the two target complementary sections. It is preferred that the length of the amplicon corresponds to the length of the connected probe, preferably minus the length provided by the two clamp sections of the first and second probe. It is more preferred that the length of the amplicon is indicative of the ligation of the corresponding first and second probes. Preferably an amplicon is a monomeric representation of the amplified connected probe.

The various embodiments of the present invention will provide further detail in this respect.

Selective Primers

In a particular preferred embodiment, one or more of the primers used in the amplification step of the present invention is a selective primer. A selective primer is defined herein as a primer that, in addition to its universal sequence which is complementary to a primer binding site that is present in all or most of the first or second probes, contains a region that comprises so-called "selective nucleotides" and which are preferably present only in a subset of the probe pairs. The region containing the selective nucleotides is located at the 3'-end of the universal primer.

The principle of selective nucleotides is disclosed inter alia in EP-A 534 858 and in Vos et al., Nucleic Acid Research, 1995, vol. 23, 4407-4414. The selective nucleotides are complementary to the nucleotides in the (ligated) probes that are located adjacent to the primer sequence. The selective nucleotides generally do not form part of the region in the (ligated) probes that is depicted as the universal primer sequence. Primers containing selective nucleotide are denoted as +N primers, in which N stands for the number of selective nucleotides present at the 3'-end of the primer. N is preferably selected from amongst A, C, T or G.

N may also be selected from amongst various nucleotide alternatives, i.e. compounds that are capable of mimicking the behaviour of ACTG-nucleotides but in addition thereto have other characteristics such as the capability of improved hybridisation compared to the ACTG-nucleotides or the capability to modify the stability of the duplex resulting from the hybridisation. Examples thereof are PNAs, LNAs, inosine etc. When the amplification is performed with more than one primer, such as with PCR using two primers, one or both primers can be equipped with selective nucleotides. The number of selective nucleotides may vary, depending on the species or on other particulars determinable by the skilled man. In general the number of selective nucleotides is not more than 10, but at least 5, preferably 4, more preferably 3, most preferred 2 and especially preferred is 1 selective nucleotide.

A +1 primer thus contains one selective nucleotide, a +2 primer contains 2 selective nucleotides etc. A primer with no selective nucleotides (i.e. a conventional primer) can be depicted as a +0 primer (no selective nucleotides added). When a specific selective nucleotide is added, this is depicted by the notion +A or +C etc.

By amplifying a pair of (ligated) probes with a selective primer, a subset of (ligated) probes is obtained, provided that the complementary base is incorporated at the appropriate position in the desired subset of the probes that are supposed to be jointly selectively amplified using the selective primer in this fashion, other subsets may optionally be selectively amplified using other combinations of selective primers. Using a +1 primer, for example, the multiplex factor of the amplified mixture is reduced by a factor 4 compared to the mixture of ligated probes prior to amplification. Higher reductions can be achieved by using primers with multiple selective nucleotides, i.e. 16 fold reduction of the original multiplex ration is obtained with 2 selective nucleotides etc and different subsets can also be achieved by different combinations of selective bases on one of the probes (e.g. +2/+0 and +0/+2).

When an assay is developed which, after ligation, is to be selectively amplified, it is preferred that the probe contains the complementary nucleotide adjacent to the primer binding sequence. This allows for pre-selection of the ligated probe to be selectively amplified.

The use of selective primers in the present invention has proven to be advantageously when developing ligation based assays with high multiplex ratios of which subsequently only a specific subset needs to be analyzed resulting in further cost reduction of the ligation reaction per datapoint. By designing primers together with adjacent selective nucleotides, the specific parts of the sample that are to be amplified separately can be selected beforehand.

One of the examples in which this is useful and advantageous is in case of analysis of samples that contain only minute amounts of DNA and/or for the identification of different (strains of) pathogens. For example, in an assay directed to the detection of various strains of anthrax (*Bacillus anthracis*), for each of the strains a pair of representative probes is designed. The detection of the presence or absence of this pair (or a characterising portion thereof) of ligated probes after the hybridisation and ligation steps of the method of the invention may serve as an identification of the strain concerned. The selective amplification with specifically designed primers (each selective primer is linked to a specific strain) can selectively amplify target sequences derived from/ of the various strains, allowing their identification by detecting the resulting amplicons. For instance, amplification with an +A primer selectively amplifies the ligated probes directed to strain X where a +G primer selectively amplifies the ligated probes directed to strain Y. If desired, for instance in the case of small amounts of sample DNA, an optional first amplification with a +0 primer will increase the amount of ligated probes, thereby facilitating the selective amplification.

For example, a universal primer of 20 nucleotides becomes a selective primer by the addition of one selective nucleotide at its 3' end, the total length of the primer now is 21 nucleotides. See in this respect also FIG. 15. If however it is desired to keep the total length of the primers constant, the universal primer can be shortened at its 5' end by the number of selective nucleotides added at the 3' end. For instance, adding two selective nucleotides at the 3' end of the primer sequence can be combined with the absence (or removal) of two nucleotides from the 5' end of the universal primer, compared to the original universal primer. Thus a universal primer of 20 nucleotides is replaced by a selective primer of 20 nucleotides. The use of selective primers based on universal primers has the advantage that amplification parameters such as stringency and temperatures may remain essentially the same for amplification with different selective primers or vary only to a minor extent. Preferably, selective amplification is carried out under conditions of increased stringency compared to non selective amplification. With increased stringency is meant that the conditions for annealing the primer to the ligated probe are such that only perfectly matching selective primers will be extended by the polymerase used in the amplification step. The specific amplification of only perfectly matching primers can be achieved in practice by the use of a so-called touchdown PCR profile wherein the temperature during the primer annealing step is stepwise lowered by for instance 0.5° C. to allow for perfectly annealed primers. Suitable stringency conditions are for instance as described for AFLP amplification in EP 0 534 858 and in Vos et al., Nucleic Acid Research, 1995, vol. 23, 4407-4414. The skilled man will, based on the guidance find ways to adapt the stringency conditions to suit his specific need without departing from the gist of the invention.

One of the further advantages of the selective amplification of ligated probes is that an assay with a high multiplex ratio can be adapted easily for detection with methods or on platforms that prefer or require a lower multiplex ratio.

Detection

The amplicons or connected probes of the present invention can be detected on a suitable detection platform. The discrimination between amplicons or connected probes derived from different target sequences can be based on length, sequence or mass as the primary parameter. Detection of the (labelled) samples is performed by a detector to result in detection data. The detector is of course dependent on the general system on which the separation is carried out (length, mass or sequence or a combination thereof) but is, if applicable, also depending on the label that is present on the primer, such as a fluorescent or a radioactive label.

Examples of suitable detection platforms are length based detection platforms, sequence based detection platforms and mass based detection platforms.

Length Based Detection

One of many examples of length based detection is the detection based on electrophoresis (capillary electrophoresis, slab-gel electrophoresis, fixed detector-continuous gel-electrophoresis) and preferably capillary electrophoresis such as is performed on MegaBACE equipment available from Molecular Dynamics Amersham-Biosciences, or using nanotechnology such as Lab-on-a-Chip or other micro-eluidic devices. The difference in length of the amplicon being detected can be provided by the use of a stuffer.

The amplicons in a sample are preferably analysed on an electrophoretic device. The electrophoretic device preferably separates the different amplicons in an amplified sample on the basis of length, after which the separated amplicons may be detected as described herein. The electrophoretic device preferably is a multichannel device in which multiple samples are electrophoresed in multiple channels, preferably in parallel. The electrophoretic device has an application location (per channel) for application (loading) of the amplified sample to be electrophoresed, a separation area over which the fragments in the sample migrate by electrophoresis, and preferably also a detection device located at a detection location distal from the application location. The detection device will usually comprises a photomultiplier for the detection of fluorescence, phosphorescence or chemiluminescence. Alternatively, in the case of gel-electrophoresis, the separated fragments may be detected in the gel e.g. by autoradiography or fluorography. Length discrimination To discriminate between different target sequences in the sample preferably a difference in length of the respective corresponding amplicons is used. By separating the amplicons based on length, the presence of the corresponding target sequences in the sample can be determined. Accordingly, in a preferred embodiment of the present invention, the discrimination between amplicons derived from different target sequences in a sample is based on a length difference between the respective amplicons corresponding to different target sequences in a sample or amplified sample.

Preferably, the length difference is provided by the length of the stuffer sequence(s) in the oligonucleotide probes of the invention. By including in at least one of the oligonucleotide probes of the pair of the invention, but preferably in both probes of the pair a stuffer of a pre-determined length, the length of each amplified connected probe in an amplified sample can be controlled such that an adequate discrimination based on length differences of the amplicons obtained is enabled. In a preferred embodiment of a probe of the pair according to the invention, the stuffer is located between the probe's section complementary to the target sequence and the primer-binding sequence. As such, the total length of the stuffer is provided by the combination of the length of the stuffer in the first probe and the length of the stuffer in the second probe. Accordingly, in a preferred embodiment, both the first oligonucleotide probes and the second oligonucleotide probes comprise a stuffer. The length differentiation between amplicons obtained from target sequences in the sample is preferably chosen such that the amplicons can be distinguished based on their length. This is accomplished by using stuffer sequences or combinations of stuffer sequences in the first and/or second probes of the pair of probes, which (together) result in length differences that may be distinguished on electrophoretic devices. Thus, from the perspective of resolving power, the length differences between the different amplified connected probes, as may be caused by their stuffers, are as large as possible. However, for several other important considerations, as noted hereinbefore, the length differences between the different amplicons is preferably as small as possible: (1) the upper limit that exists in practice with respect to the length of chemically synthesised probes of about 100-150 bases at most; (2) the less efficient amplification of larger fragments, (3) the increased chances for differential amplification efficiencies of fragments with a large length variation; and (4) the use of multiple injections of detection samples on the detection device which works best with fragments in a narrow length range. Preferably the length differences between the sequences to be determined and provided by the stuffers is at least sufficient to allow discrimination between essentially all amplified connected probes. By definition, based on chemical, enzymatic and biological nucleic acid synthesis procedures, the minimal useable size difference between different amplicons in an amplified sample is one base, and this size difference fits within the resolving power of most electrophoresis devices, especially in the lower size ranges. Thus based on the above it is preferred to use multiplex assays with amplification products with differ in length by a single base(pair). In a preferred embodiment, the length difference between different amplicons in an amplified sample is at least two nucleotides. In a particularly preferred embodiment of the invention the amplicons corresponding to different target sequences in a sample have a length difference of two nucleotides.

Length and Label

Throughput can be increased by the use of multiple labelled primers. One of the problems associated with the use of different labels in one sample is cross talk or residual cross talk. Cross talk or residual cross talk, as used herein, refers to the overlap between the emission spectra of different (fluorescent) labels. For instance when fluorescent dyes are used, each dye has a different emission (and absorption) spectrum. In case of two dyes in one sample, these spectra can overlap and may cause a disturbance of the signal, which contravenes the quality of the data obtained. Particularly when two nucleotide fragments to be detected in a sample are labelled with a different label and one of the fragments is present in an abundant amount whereas the other is present only in minute amounts, residual cross talk can cause that the measured signal of the fragment that is present in only minute amounts is mostly derived from the emission of another label with an overlapping emission spectrum that is abundantly contained in a fragment with identical size of another sample. The reciprocal effect of the other dye may also occur but in this example its effect is probably less because of the abundance differences between the amplicons labelled with the respective dyes.

Chehab et al. (Proc. Natl. Acad. Sci. USA, 86:9178-9182 (1989) have attempted to discriminate between alleles by attaching different fluorescent dyes to competing alleles in a single reaction tube by selecting combinations of labels such that the emission maximum of one dye essentially coincides with the emission minimum of the other dye. However, at a certain wavelength at which one dye expresses an absorption maximum, there is always also some remaining absorption from another dye present in the sample, especially when the sample contains multiple dyes.

This route to multiplex analysis was found to be limited in scale by the relatively few dyes that can be spectrally resolved. One of the major problems with the use of multiple dyes is that the emission spectra of different fluorescent labels often overlap. The resulting raw data signals have to be corrected for the contribution of similar size fragments that are detected simultaneously and are labelled with another fluorescent dye by a process called cross-talk correction. Cross-talk correction is commonly carried out by mathematical means, based on the known theoretical absorption spectra for both dyes, after "raw" data collection from the detection device. Mathematical correction is based on theoretical spectra and ignores that emission spectra of labels are sensitive and often affected by the composition of the detection sample. These sensitivities can affect the brightness and/or the wavelength of the emission. This means that parameters such as pH, temperature, excitation light intensity, non-covalent interactions, salt concentration and ionic strength strongly influence the resulting emission spectrum. In particular, it is known that the presence of residual salts in a sample affects the fluorescence signal emitted by the dye and is a critical factor in case of detection by capillary electrophoresis using electrokinetic injection because it then also affects the injection efficiency. Thus, spectral overlap is a potential source of error that negatively impacts on data quality in case of multiplex detection using different fluorescent dyes.

The present invention provides for a solution to this problem such that two (or more) labels with overlapping spectra can be used in the same sample without significantly affecting data quality. By a predetermined combination of length differences and labels, an increase in the number of target nucleotide sequences that can be detected in sample is obtained while the quality of the data remains at least constant. In a preferred embodiment of the invention, spectral overlap between two differently labelled sequences is reduced by the introduction of a length difference between the two sequences. This label-related length difference can be provided for by the length of the stuffer sequence as described herein. The number of different labels that can be used in the same sample in the present method is at least two, preferably at least three, more preferably at least four. The maximum number of labels is functionally limited by the minimum of spectral overlap that remains acceptable, which for most applications typically amounts to less than 15 percent of the true signal, preferably less than 10 percent, more preferably less than 5 percent and most preferably less than 1 percent of the true signal.

In order to avoid the potential influence of residual cross-talk on the data quality in case different samples are labelled with multiple fluorescent dyes with overlapping emission spectra and fragments with identical length are detected simultaneously in the same run, in a particular preferred embodiment it is preferred to choose the stuffer sequences such that amplicons differ by at least two base pairs within a multiplex set and differ by a single base pair between multiplex sets labelled with the different dyes that have overlapping spectra. By doing so, the length of the fragments labelled with the respective dyes can be chosen such that the potential influence of residual cross-talk on the quality of the data is circumvented because unique combinations of fragments size and labelling dye are defined.

A particular preferred embodiment of the invention is directed to a method in which a sample comprising amplicons is derived from a multiplicity of target sequences. These amplicons are differently labelled, thereby defining groups of amplicons carrying the same label. Within each group, the stuffer provided for a length difference of at least two, preferably two nucleotides. Between two groups with labels having spectral overlap, the stuffer provides a length difference of one nucleotide, effectively resulting in one group having an even number of nucleotides and one group having an odd number of nucleotides as described above.

In one aspect the present invention pertains to a method for the improved discrimination and detection of target sequences in a sample, comprising providing at least a two or more groups of oligonucleotide probes, wherein the amplicons obtained with different groups of oligonucleotide probes have different labels, wherein substantially each amplified connected probe within a group has the same label, wherein within a group of identically labelled amplicons a length difference is provided between each identically labelled probe within that group, wherein between the first and second group an additional length difference is provided such that each amplified connected probe in the amplified sample is characterised by a combination of length of the sequence and the label.

In a preferred embodiment of the method of the invention, at least two groups of pairs of first and second oligonucleotide probes are provided to a sample, whereby each group of oligonucleotide probes has tag sequences with at least one group specific primer-binding site. The connected probes of each group are amplified from a primer pair wherein at least one of the first and second primers is complementary to the group specific primer-binding site, and whereby at least one of the first and second primers of a group comprises a group specific label. In each group, an amplicon corresponding to a target sequence in the sample, differs in length from an amplicon corresponding to a different target sequence in the sample. The group specific labels are preferably such that the detection device can distinguish between the different group specific labels. The length difference is preferably provided by the length of the stuffer sequence. Preferably in this embodiment of the method of the invention, a first part of the groups has amplicons having an even number of nucleotides and a second part of the groups has amplicons having an odd number of nucleotides. Preferably, the groups of amplicons having an even number of nucleotides and the groups amplicons having an odd number of nucleotides are labelled with (fluorescent) labels, which have the least overlap in their emission spectra. Thus, two groups of amplified connected probes, each group having an odd number of nucleotides are labelled with labels which have the least overlap in their emission spectra. The same holds for two groups of amplified connected probes, each group having an even number of nucleotides. Two groups of amplified connected probes, one group having an odd number of nucleotides and the other group having an even number of nucleotides are labelled with labels that have a larger overlap in their emission spectra. The relative notions as used herein of 'the least overlap in their emission spectra' and 'have a larger overlap in their emission spectra' refer to a group of labels from which a selection of the labels can be made for use in the present invention. This group of labels may depend on the detection platform used to other factors such as those disclosed herein before. In a particularly preferred embodiment of this method, a first and second groups of amplicons having an even number of nucleotides are produced and a third and fourth group of connected amplified probes having an odd number of nucleotides are produced and whereby the first and second group are labelled with FAM and NED, respectively, and the third and fourth group are labelled with (ET-)ROX and either JOE or HEX, respectively; or vice versa, whereby the first and second group are labelled with (ET-)ROX and either JOE or HEX, respectively, and the third and fourth group are labelled with FAM and NED, respectively. Thus, in these embodiments, the fluorescent labels are chosen such that the groups of amplicons that co-migrate, because they both contain fragments with either even or odd numbers of nucleotides, have labels which have the least overlap in their emission spectra, thereby avoiding as much as possible cross-talk in the detection of amplicons in different groups (see also below).

In a preferred embodiment to avoid cross-talk it is therefore desirable to combine a difference in length with a different label when analysing a set of amplicons in such a way that the influence of spectral overlap on the data quality is avoided by length differences between the amplicons labelled with the dyes that have overlapping emission spectra It is preferred that in each sample the connected probes derived from each target sequence differ from any other connected probe in the sample in length, and/or in the label or, preferably in the combination of the length and the label. To provide for an adequate separation of the amplicons of different length it is preferred that the length difference between two different connected probes is at least two nucleotides, preferably two. When detecting polymorphisms it is preferred that the difference in length between two or more (SNP) alleles of the polymorphism is not more than two, thereby ensuring that the efficiency of the amplification is similar between different alleles or forms of the same polymorphism. This implies that preferably both alleles are amplified with the same pair of primers and hence will be labelled with the same dye.

In a preferred embodiment, for example directed to the detection of different alleles of a multiplicity of loci, the distribution between odd/even lengths within a group can be designed in the following way. Two loci L1, L2 are each represented by two alleles A11, A12 for L1 and A21, A22 for L2. The lengths of the various alleles (or ligated and amplified probes representing those alleles) is such that A11>A12>A21>A22; A12−A11=2; A22−A21=2; A12−A21=3. Between groups G1 and G2 carrying labels that may have an overlap in their spectra there can be a length difference of 1 nucleotide. Thus G1(A11)−G2(A11)=1, hence the group starts with either an even or an uneven length.

This distribution has some significant advantages compared to the more densely packed distribution disclosed herein. It is known that due to conformational differences that different sequences of identical length generally differ in their electrophoretic mobility. When there is only a difference in length of one nucleotide, this may cause overlap between the peaks if the sequences are of a very different mobility. For instance the difference in mobility between two alleles of one locus (A11, A12), will be less than the difference in mobility between two alleles from different loci (A12, A21). When there is a significant difference in mobility between A12 and A21, this may lead to unreliable detection. By creating length distributions as herein disclosed this can be avoided. The lower throughput is then weighed against the reliability of the detection.

The problem of the overlap between the spectra of the different labels is then adequately avoided. This is schematically depicted in Table A.

TABLE A

Alternative distribution scheme of labels and lengths of probes.

| Length | Group 1-Label 1 | Group 2-Label 2 | Group 3-Label 3 | Group 4-Label 4 |
|---|---|---|---|---|
| N | G1A11 | | G3A11 | |
| N + 1 | | G2A11 | | G4A11 |
| N + 2 | G1A12 | | G3A12 | |
| N + 3 | | G2A12 | | G4A12 |
| N + 4 | | | | |
| N + 5 | G1A21 | | G3A21 | |
| N + 6 | | G2A21 | | G4A21 |
| N + 7 | G1A22 | | G3A22 | |
| N + 8 | | G2A22 | | G4A22 |
| N + 9 | | | | |
| N + 10 | G1A31 | | G3A31 | |
| N + 11 | | G2A31 | | G4A31 |
| N + 12 | G1A32 | | G3A32 | |
| N + 13 | | G2A32 | | G4A32 |
| N + 14 | | | | |
| N + 15 | G1A41 | | G3A41 | |
| N + 16 | | G2A41 | | G4A41 |
| N + 17 | G1A42 | | G3A42 | |
| N + 18 | | G2A42 | | G4A42 |

In an embodiment of the present invention there is provided between the amplicons within one group, a length difference of alternating two and three nucleotides, i.e. 0, 2, 5, 7, 10, 12 etc. The other group then has a length difference of 1, 3, 6, 8, 11, 13 etc. Based on the information disclosed herein, the skilled man may determine other ways of varying length differences within a range.

Multiple Injection

In order to come to a high throughput method of a multiplex of samples, a number of samples are treated similar to thereby generate a multiplicity of amplified detection samples which can then be analysed on a multichannel device which is at least capable of detecting the labels and/or length differences. Suitable devices are described herein above.

To increase throughput on electrophoretic platforms methods have been developed that are described in this application and are commonly depicted as multiple injection. By injecting multiple samples containing fragments of discrete, predetermined lengths, in the same electrophoretic matrix and/or in short consecutive runs, throughput can be increased. All detectable fragments preferably have a length within a specific span and only a limited number of fragments can be detected in one sample, hence the advantage of selective amplification for the reduction of the multiplex ratio by the selection of a subset of the connected probes in the amplification step resulting in a subset of amplicons.

The methods of the present invention may be performed on two or more nucleic acid samples, each containing two or more different target nucleic acids, to produce two or more amplified samples in which is presence or absence of connected and amplified probes is analysed.

The multiplex analysis of the amplified samples following the method of the invention comprises applying at least part of an amplified sample to an electrophoretic device for subsequent separation and detection. Preferably such an amplified sample contains, or is at least suspected to contain, amplified connected probes, which is an indication that a target sequence has hybridised with the provided oligonucleotide probes and that those probes were annealed adjacently on the complementary target sequence so that they where connected, i.e. ligated. Subsequently, an amplified sample is subjected to a separating step for a selected time period before a next amplified sample is submitted.

In the method of the invention, (parts of) two or more different amplified samples are applied consecutively to the same channel of the electrophoretic device. Depending on the electrophoresis conditions, the time period between two (or more) consecutively applied amplified samples is such that the slowest migrating amplified connected probe in an amplified sample is detected at the detection location, before the fastest migrating amplified connected probe of a subsequently applied amplified sample is detected at the detection location. Thus, the time intervals between subsequent multiple injections in one channel of the device are chosen such that consecutively applied samples after separation do not overlap at a point of detection.

The method according to the invention allows for the high throughput analysis of a multiplicity of samples each comprising a multiplicity of different target sequences by the consecutive injection of amplified samples, comprising amplified connected probes corresponding to the target sequences in the samples, in a channel of a multichannel electrophoretic device such as a capillary electrophoresis device. The method according to the invention allows for the analysis of a multiplicity of target sequences in a multiplicity of samples on a multiplicity of channels, thereby significantly increasing the throughput of the number of samples that can be analysed in a given time frame compared to conventional methods for the analysis of nucleotide sequences. This method profits from samples containing amplicons to be detected that are of a discrete size range as thereby the time period between the successive injections can be significantly reduced compared to methods in which no use is made of samples that contains sequences to be detected that are not within a discrete size range.

The selected time period prevents that consecutively applied samples after separation have an overlap of connected probes at the detection point. The selected time period is influenced by i). the length of the amplified connected probes; ii). the length variation in the amplified connected probes; and iii). the detection device and its operating conditions. Applying samples and separating consecutively applied samples in the same channel can be repeatedly performed in one or more channels, preferably simultaneously to allow for consecutive electrophoretic separation of multiple samples in one channel and/or simultaneous analysis of multiple samples over multiple channels and/or simultaneous analysis of multiple samples over multiple channels carried out consecutively.

The period of time between two consecutively loaded amplified samples can be determined experimentally prior to executing the method. This period of time is selected such that, given the characteristics of an amplified sample, especially the difference in length between the shortest and the longest amplified connected probes in an amplified sample, as well as other experimental factors such as gel (matrix) and/or buffer concentrations, ionic strength etc., the fragments in an amplified sample are separated to such extent at the detection location which is located at the opposite end (distal) from the application location where the sample was applied, that the different amplified connected probes in a sample may be individually detected. After applying the last amplified sample, the separation can be continued for an additional period of time to allow the amplified connected probes of the last sample to be separated and detected. The combination of the selected period of time between applying two consecutive samples and the optional additional time period is chosen such that at the detection location the different amplified connected probes in consecutively applied samples are separated such that they may be individually detected, despite the limited length variation that exists between the different amplified connected probes within a single sample. Thus overlapping migration patterns are prevented when samples containing fragments of varying length are consecutively applied (injected) on the electrophoretic device.

Using the method according to the invention, it is in principle possible and preferred to continuously apply, load or inject samples. Preferably the device is able to perform such operation automatically, e.g. controlled by a programmable computer. Preferably the multichannel device is suitable for such operation or is at least equipped for a prolonged operation without maintenance such as replacement of buffers, parts etcetera. However, in practice this will generally not be the case. When a final sample is submitted it is generally needed to continue the separation for an additional time period until the last fragment of the final sample has been detected.

In a preferred embodiment of the invention, the stuffers present in both the first and second oligonucleotide probes of the pair of the invention are used to provide the length differences (i.e. 0 to 500 nucleotides, bases or base pairs) between the amplified connected probes. The total length of the amplified connected probes and the variation in the length is governed mostly by the techniques by which these fragments are analysed. In the high throughput multiple injection method of the present invention, it is preferred that the range of lengths of amplified connected probes in an amplified sample has a lower limit of 40, 60, 80, or 100 and an upper limit of 120, 140, 160, or 180 nucleotides, bases or base pairs, for conventional (capillary) electrophoresis platforms. It is particularly preferred that the range of lengths of the amplified connected probes varies from 100 to 140 nucleotides. However, these number are strongly related to the current limits of the presently known techniques. Based on the knowledge provided by this invention, the skilled artisan is capable of adapting these parameters when other circumstances apply.

The reliability of the multiplex amplification is further improved by limiting the variation in the length of the amplified connected probes. Limitations in the length variation of amplified connected probes is preferred to use multiple injection more efficiently and further results in reduction of the preferential amplification of smaller amplified connected probes in a competitive amplification reaction with larger connected probes. This improves the reliability of the high throughput method of the present invention. Together with the multiple injection protocol as herein disclosed, these measures, alone or in combination provide for a significant increase in throughput in comparison with the art. A further improvement of the high throughput capacity is obtained by limiting the number of different amplified connected probes in a sample. It is regarded as more efficient and economical to limit the multiplex capacity of the ligation/amplification step in combination with the introduction of a multiple injection protocol. One of the most advantageous aspects of the present invention lies in the combination of the innovative pair of probes, multiplex ligation, multiplex amplification, preferably with a single primer pair or with multiple primer pairs which each amplify multiple connected probes, repeated injection and multiplex detection of different labels, optionally in combination with selective priming that allows for the flexibility in multiplex ratio between ligation and amplification steps. One of the further advantageous aspects of the present invention resides in the combined application of length differences with different (overlapping) labels such that each connected probe and hence each target sequence within one sample can be characterised by a unique combination of length and label. This allows for a significant improvement of the efficiency of the analysis of target sequences as well as a significant reduction in the costs for each target analysed.

The multiple injection protocol can be performed in a variety of ways. One of these ways is the multiple loading of two or more samples in the same matrix. This is considered as advantageously as the matrix is re-used by performing consecutive short runs, thereby increasing efficiency and throughput. Another way is the multiple loading of two or more samples in the same matrix in the same run. It is preferred to re-use the matrix by performing short consecutive runs. In this embodiment, a first sample is injected and separated. As soon as the last fragment is detected, the next sample is loaded. Preferably, between these two consecutive short runs the matrix is not replaced so that the runs are performed in the same matrix. This provides for additional efficiency and improved economics as less changes o the matrix need to occur, reducing the amount of consumables of this type of analysis (i.e. buffers etc.), reducing the cost per datapoint. Furthermore time-consuming replacements of the matrix can be avoided to a large extent, further increasing the efficiency of the method.

In itself, certain aspects of multiple loading or multiple injection have been described inter alia in U.S. Pat. No. 6,156,178 and WO 01/04618. The latter publication discloses an apparatus and a method for the increased throughput analysis of small compounds using multiple temporally spaced injections. The publication discloses that samples comprising primers, extended by one nucleotide (single nucleotide primer extension or SnuPE, also known as minisequencing) could be detected using multiple temporally spaced injections on a capillary electrophoresis device. Minisequencing is based on annealing a complementary primer to a previously amplified target sequence. Subsequent extension of the primer with a separately provided labelled nucleotide provides for identification of the nucleotide adjacent to the primer. Principally, the primer extension product is of a constant length. To increase throughput the use of successive injections of extension products of the same length per run is suggested. To further increase the throughput, primers of a different length can be used, varying typically from 15 to 25 nucleotides. In contrast, the present invention contemplates analysing multiplex amplification products themselves directly with a length variation typically between 50 and 150 nucleotides. This is significantly more economical than minisequencing or SnuPE as outlined hereinbefore because multiple target sequences are amplified in a single reaction, whereas with minisequencing or SnuPE amplification is carried out individually for each target sequence. Furthermore, the use of primers of a different length and complementary to the target sequence compromises the efficiency of the subsequent amplification step needed in the method of the present invention.

The efficiency of the present invention can be illustrated as follows. When a capillary electrophoretic device with 96 channels and capable of detecting four labels simultaneously is used, allowing for 12 subsequent injections per run per channel with a empirically optimised minimum selected time period between the injections, a sample containing 20 target sequences of interest allows for the high throughput detection of 96 (channels)*12 (injections)*20 (targets)*4 (labels)= 92160 target sequences, using the method of the present invention. In the case of co-dominant SNP-detection, data regarding 46080 SNPs can be detected in a single run.

Size Ladder

The sample can be supplied with a nucleotide fragment size standard comprising one or more nucleotide fragments of known length. Methods of preparing and using nucleotide size standards are well known in the art (see e.g. Sambrook and Russel, 2001, supra). Such a size standard forms the basis for appropriate sizing of the amplicons in the sample, and hence, for the proper identification of the detected fragment. The size standard is preferably supplied with every sample and/or with every injection. A size standard preferably contains a variety of lengths that preferably spans the entire region of lengths to be analysed. In a particular embodiment of the invention, it is considered advantageously to add flanking size standards from which the sizes of the amplicons can be derived by interpolation. A flanking size standard is a size standard that comprises at least two labelled oligonucleotide sequences of which preferably one has a length that is at least one base shorter than the shortest amplified connected probe and preferably one that is a least one base longer than the longest amplified connected probe to allow interpolation and minimise the introduction of further length variation in the sample. A preferred flanking size standard contains one nucleotide that is one nucleotide shorter the shortest amplified connected probe and one that is a least one base longer than the longest amplified connected probe and is labelled with at least one dye that is identical to the label used for labelling the amplicons contained in the sample.

A convenient way to assemble a suitable size standard is by (custom) chemical synthesis of oligonucleotides of the appropriate lengths, which are end-labelled with a suitable label. The size standard is applied with every consecutively applied sample to serve as local size references to size the loaded sample fragments. The size standard may be applied in the same channel or lane of the electrophoretic device as the sample to be analysed, i.e. together with the sample, or may be applied in a parallel channel or lane of a multichannel/lane device. The flanking size standard can be labelled with any of the labels used in the method. If the size standard is applied in the same channel of the device, the fragments of the standard are preferably labelled with a label that can be distinguished from the labels used for the detection of the amplicons in a sample.

Sequence Based Detection

Examples of sequence based detection platforms are solid phase and fluid phase microarrays. Preferably, uniquely addressable arrays are used wherein the probe contains a unique sequence (such as a ZIP sequence) thereby providing that the ligated (and amplified probe ) will hybridise to a predetermined spot on the array wherein the complementary ZIP sequence is located (cZIP). Array-based detection methods are commonplace nowadays and the technology is widely spread, allowing the skilled man to create a suitable array for the detection of the ligated pairs of probes of the present invention.

Mass Based Detection

An example of mass based platforms is MALDI-TOF. The analytes to be detected each have a different mass. This can be achieved for instance by the incorporation of a stuffers sequence comprising a restriction site in (one of) the probes. When the ligated probes are restricted prior to detection (optionally after amplification), a set of fragments/oligonucleotides are obtained, each having a different mass that is associated with the presence or absence of a target sequence in the sample.

One embodiment of the invention using mass based detection relates to a method for determining the presence or absence of a target sequence in a nucleic acid sample, wherein the presence or absence of the target sequence is determined by an oligonucleotide ligation assay in combination with a detection method based upon molecular mass and wherein each target sequence in the sample is represented by a stuffer and detection of the target sequences is based on the detection of the presence or the absence of a fragment comprising said stuffer.

A preferred aspect of the invention pertains to a method for determining the presence or absence of at least one target sequence (2) in a nucleic acid sample, comprising the steps of:

providing to a nucleic acid sample a pair of a first and a second oligonucleotide probe according to the invention for each target sequence to be detected in the sample, whereby the first oligonucleotide probe has a section at its 5'-end that is complementary to a first part of a target sequence and the second oligonucleotide probe has a section at its 3'-end that is complementary to a second part of the target sequence, whereby the first and second part of the target sequence are preferably located adjacent to each other, and whereby one or more of the first and second oligonucleotide probes further comprise one or more primer-binding sequences and one or more stuffers and a restriction site for a restriction enzyme, which restriction site is located between the primer binding site and the section of the oligonucleotide probe that is complementary to the first or second part of the target sequence and wherein the stuffer is located between the restriction site and the primer binding site and wherein the first oligonucleotide probe comprises a first clamp section, that is capable of hybridising to a second clamp section of the second oligonucleotide probe and wherein the second oligonucleotide probe comprises a second clamp section, that is capable of hybridising to the first clamp section of the first oligonucleotide probe;

allowing the oligonucleotide probes to anneal to the adjacent parts of target sequence whereby the complementary sections of the first and the second oligonucleotide probes are adjacent;

providing means for connecting the first and the second oligonucleotide probes annealed adjacently to the target sequence and allowing the complementary sections of the adjacently annealed first and second oligonucleotide probes to be connected, to produce a connected probe corresponding to a target sequence in the sample;

amplifying the connected probes from a primer pair to produce an amplified sample comprising amplified connected probes;

digesting the amplified connected probes with the restriction enzyme to produce a detectable fragment;

detecting the presence or absence of the target sequence by detecting the presence or absence of the detectable fragment by a detection method based upon molecular mass.

In step (e) the amplified connected probes are cleaved or cut. Cleaving the amplified connected probes can be achieved by any suitable means known in the art as long as a reproducible cleaved or cut nucleotide strand is obtained. Reproducible in this respect refers to the preference that the means for cleaving or cutting cut the nucleotide sequence at the same position in the sequence of the amplified connected probes. The means for cleaving the amplified connected probe can be chemical or enzymatic, but are preferably enzymatic, such as a restriction enzyme. A preferred restriction enzyme is a restriction endonuclease. An amplified connected probe is preferably cleaved by the restriction enzyme at the restriction site that was provided in the tag of one of the probes. Cleaving the amplified connected probes produces either flush ends in which the terminal nucleotides of both strands resulting from the restriction step are base-paired, or staggered ends in which one of the ends resulting from the restriction step protrudes to give a (short) single strand extension. Preferably the restriction site is recognised by a sequence specific restriction endonuclease. In principle any restriction endonuclease known in the art can be used, as long as it produces a reproducible cut. Cleaving the amplified connected probes in the sample results in a detectable fragment.

Restriction endonucleases itself are widely known in the art. A suitable restriction enzyme can have a recognition sequence of 4, 5, 6, 7, or 8 or more nucleotides. Preferably the restriction endonuclease is a rare cutter, (i.e. has a recognition sequence of more than 4 nucleotides). Preferably the restriction enzyme is a type II enzyme or a type IIs enzyme. Preferred restriction enzymes are EcoRI, HindIII, BamHI. Other preferred restriction enzymes are 6-cutter restriction enzymes, preferably 6-cutters that are relatively inexpensive.

Digesting amplified connected probes in step (e), for instance with restriction endonucleases, results in detectable fragments (comprising the stuffer sequence) and the remains of the amplified connected probes (waste fragments). The waste fragments, comprise the ligated complementary sections. Digesting with a restriction endonuclease results in a detectable fragment which is double stranded. Both the detectable fragments and the waste fragments consist of two strands, one designated as the top strand and the other as the bottom strand. The detectable fragment can be subjected to a denaturation treatment to provide for the separate bottom strand and top strands. The bottom strand is essentially complementary to the top strand, i.e. the largest part of the nucleotide sequence of the top and bottom strand are complementary, with the exception of those nucleotides that are part of a staggered or sticky end, essentially as described hereinbefore. Either the top or the bottom strand can be detected, or both the top and the bottom strand.

Detection is based on the detection of the presence or absence of the detectable fragment. Detection of the detectable fragment is preferably indicative of the presence or absence of the amplified connected probes in the amplified sample and hence of the target nucleotide sequence in the nucleic acid sample. Preferably the detection is based on the detection of the top and/or the bottom strand of the detectable fragment. The detection of the bottom strand in addition to the top strand has the advantage that direct confirmation of the presence or absence of the target sequence is obtained in duplo.

The detection can be performed directly on the digested sample, but it is preferred that, prior to detection, the detectable fragment is isolated, purified or separated from the digested amplified connected probes. The detectable fragment can be isolated, purified or separated from the digested amplified connected probes by means known in the art such as spin column purification, reversed phase purification or, preferably by affinity labelling techniques such as a biotin-streptavidin combination, combined with a suitable carrier such as magnetic beads, probe sticks etc. Isolation, purification or separation can also be performed after a denaturation treatment on the top and/or bottom strands.

The detectable fragment is preferably labelled with an affinity label. The affinity label is preferably located at the extreme end of the detectable fragment, located distal from the restriction site or, after digestion, the remains of the restriction site. The top strand and/or the bottom strand of the detectable fragment can be equipped with the affinity label. Preferably it is the bottom strand that comprises the affinity label and the stuffer sequence. The notion top strand is generally used to indicate that the nucleotide sequence of the top strand at least in part corresponds to the part of the tag that comprises the stuffer, the restriction site and the primer binding site, i.e. the top strand contains a nucleotide sequence that is essentially identical to that of the probe. The bottom strand is the strand complementary to the top strand and is obtained after a first round of amplification by extension of a primer complementary to the primer binding site in the top strand and which primer is preferably equipped with an affinity label. Accordingly, the bottom strand contains a sequence that corresponds to the nucleotide sequence of one of the primers. In a particular preferred embodiment the bottom strand is equipped with the affinity label. Preferably the bottom strand is isolated from the sample comprising the denatured detectable fragments, preferably by the affinity label. Preferably it is the bottom strand that is detected using mass spectrometry. Hence detection of the bottom strand provides the information relating to the presence or the absence of the corresponding target nucleotide strand.

The affinity label can be used for the isolation of the top and/or the bottom strand from the mixture of digested amplified connected probes. As an affinity label, a biotin-streptavidin combination is preferred. The affinity labelled top strand, bottom strand or detectable fragment can subsequently be detected using detection techniques based on molecular mass.

As used herein, the term affinity label also encompasses affinity labels that are coupled via so-called 'linkers' (having a certain molecular mass) located between the nucleotide sequence of the tag and the actual affinity label.

In an alternative embodiment, the affinity label is provided in the tag that does not comprise the restriction site-stuffer combination. This allows for the isolation of the amplified connected probes prior to the digestion step. The resulting mixture, after restriction and optional denaturation, can directly be analyzed using mass spectrometry. As the mass of the detectable fragments, or the top or bottom strands, is known or can at least be calculated, the waste fragments (i.e. the remains of the digested amplified connected probes) do not significantly compromise the detection as the detectable fragments, and both the top or bottom strands, are within a known and different mass range.

Detection techniques based on molecular mass are for instance mass spectrometry and more in particular the mass spectrometry techniques that are suitable for the detection of large molecules such as oligonucleotides. Examples of these techniques are matrix assisted laser desorption/ionisation time-of-flight (MALDI-TOF), HPLC-MS, GC-MS etcetera. Commonly the detection techniques based on molecular mass prefer that the submitted samples contain oligonucleotides in a single stranded form. In case the detectable fragment has been isolated as a double stranded oligonucleotide, the detectable fragment is preferably denatured, using techniques known in the art, to yield single stranded oligonucleotides for instance such as those described herein as top and/or bottom strands.

After digestion with a restriction endonuclease, the obtained detectable fragment preferably comprises a stuffer, remains of the restriction site, and the primer binding site. Optionally an affinity label can be attached to the top and/or the bottom strand, optionally via a linker. The mass to be detected hence is the summation of the molecular mass of the primer binding site, the stuffer, the remains of the restriction site and the optional affinity label and optional linker.

To distinguish between different target sequences in a nucleic acid sample, the detectable fragments are designed such that a detectable fragment corresponding to one target sequence in the sample differs in mass from a detectable fragment corresponding to another target sequence in the sample. Accordingly, a sample comprising multiple target sequences comprises (after ligation, amplification and digestion) multiple detectable fragments, each detectable fragment with a different mass. Upon denaturation of the detectable fragments in the respective top and bottom strands, the various top strands each have a different mass. Likewise, the various bottom strands each have a different mass. Preferably, the mass difference between two different detectable fragments (and hence between two top or bottom strands respectively) is provided by the difference in mass of the stuffer.

The top strand or the bottom strand can be regarded as comprising a constant section and a variable section. The constant section comprises the primer binding site, the optional affinity label (including the optional linker) and the remains of the restriction site. The variable section comprises the stuffer. The constant section is constant within one sample and is of a constant mass. The variable section preferably provides the difference in mass between strands that correspond to different target nucleotides in a sample In one embodiment of the present invention, the detectable fragment (and consequently) the oligonucleotide probes are designed such that the constant section is also varied in mass. This allows for the creation of multiple regions within a mass spectrum. Each region will have a lower limit and an upper limit, thereby defining a window. The lower limit of the window is defined by the mass of the constant sequence. By using different constant sequences, different regions can be defined. Preferably, these regions do not overlap. Within one region a mass difference between the oligonucleotides to be detected is created by the mass difference between the stuffers essentially as described herein before. The upper limit of the region is at least the sum of the lower limit of the region and the stuffer with the largest mass. For example, two constant sections have a mass of 6489 Dalton and 8214, respectively. Stuffer sequences of up to two nucleotides provide for 15 different combinations (including the absence of a stuffer, hence mass 0), each with a different molecular weight, ranging from 0 up to 642 (AG or GA). This allows for two regions, one ranging from 6489 Dalton to 7131 Dalton and one region from 8214 Dalton to 8856 Dalton. This allows for an increase of the multiplex capacity of the present invention. This also allows for the pooling of samples prior to mass analysis. Both will increase the high throughput capacity of the present invention.

To design stuffers that can be used in the probes of the present invention and that are capable of providing a unique mass to every detectable fragment and hence the top strand or bottom strand in the sample, the stuffers preferably have to meet the following requirements: i) a limited number of identical consecutive bases t6 avoid slippage of the polymerase during the amplification step; ii) no internal recognition site for the restriction enzyme; iii) minimal mass difference to ensure adequate resolution; iv) no formation of hairpins, for instance with other parts of the ligation probes for instance due to intramolecular hybridization.

Stuffers suitable for use in the invention can be designed using a method that computes all possible stuffer sequences up to a pre-determined length and that fulfill the criteria listed above (i-iv). This method can be performed using a computer program on a computer. This method can be considered as an invention in itself. The computer program can be provided on a separate data carrier such a as diskette. The method starts with providing the upper length limit of the stuffer sequence. The method subsequently calculates all possible permutations of nucleotide sequences and through a process of elimination and selection applies the criteria i-iii as listed hereinbefore. The number of allowable consecutive bases can be provided separately or can be predetermined. The recognition site for the restriction enzyme can be provided as separate input, but can also be derived from a database of known recognition sites for the restriction enzyme, depending on whether or not other the presence of recognition sequences of other restriction enzymes is allowed. The minimal mass difference can also be provided as separate input or as a predetermined parameter. The formation of hairpins can be checked by using a standard PCR-primer selection program such as Primer Designer version 2.0 (copyright 1990,1991, Scientific and Educational software). The resulting stuffer sequences can be presented to the user in a suitable format, for instance on a data-carrier.

The method according to the invention allows for the analysis of a multiplicity of target sequences thereby significantly increasing the throughput of the number of samples that can be analysed. "Throughput" as used herein, defines a relative parameter indicating the number of samples and target sequences that can be analysed per unit of time.

Pooling

In a variant of the technology, the starting (DNA) material of multiple individuals are pooled such that less detection samples containing this material are loaded on the detection device. This can be advantageous in the case of Linkage Disequilibrium (LD mapping) when the objective is to identify amplified connected probes (such as those representing SNP alleles) that are specific for a particular pool of starting samples, for example pools of starting material derived from individuals which have different phenotypes for a particular trait.

Application

One aspect of the invention pertains to the use of the method in a variety of applications. Application of the method according to the invention is found in, but not limited to, techniques such as genotyping, transcript profiling, genetic mapping, gene discovery, marker assisted selection, seed quality control, hybrid selection, QTL mapping, bulked segregant analysis, DNA fingerprinting and microsatellite analysis. Another aspect pertains to the simultaneous high throughput detection of the quantitative abundance of target nucleic acids sequences. This approach is commonly known as Bulk Segregant Analysis (BSA).

Detection of Single Nucleotide Polymorphisms

One particular preferred application of the method according to the invention is found in the detection of single nucleotide polymorphisms (SNPs). A first oligonucleotide probe of the pair according to the invention comprises a part that is complementary to a part of the target sequence that is preferably located adjacent to the polymorphic site, i.e. the single polymorphic nucleotide. A second oligonucleotide probe of the pair according to the invention is complementary to the part of the target sequence such that its terminal base is located at the polymorphic site, i.e. is complementary to the single polymorphic nucleotide. If the terminal base is complementary to the nucleotide present at the polymorphic site in a target sequence, it will anneal to the target sequence and will result in the ligation of the two probes. When the end-nucleotide, i.e. the allele-specific nucleotide does not match, no ligation or only a low level of ligation will occur and the polymorphism will remain undetected.

When one of the target sequences in a sample is derived from or contains a single nucleotide polymorphism (SNP), in addition to the probes specific for that allele, further probes can be provided that not only allow for the identification of that allele, but also for the identification of each of the possible alleles of the SNP (co-dominant scoring). To this end a combination of types of probes can be provided: one type probe that is the same for all alleles concerned and one or more of the other type of probe which is specific for each of the possible alleles. These one or more other type of probes contain the same complementary sequence but differ in that each contains a nucleotide, preferably at the end, that corresponds to the specific allele. The allele specific probe can be provided in a number corresponding to the number of different alleles expected. The result is that one SNP can be characterised by the combination of one type of probe with four other type (allele-specific) probes, identifying all four theoretically possible alleles (one for A, T, C, and G), by incorporating stuffer sequences of different lengths (preferred) or different labels into the allele specific probes.

In a particular embodiment, preferably directed to the identification of single nucleotide polymorphisms, the first oligonucleotide probe of the pair according to the invention is directed to a part of the target sequence that does not contain the polymorphic site and the second oligonucleotide probe of the pair according to the invention contains, preferably at the end distal from the primer-binding sequence, one or more nucleotide(s) complementary to the polymorphic site of interest. After ligation of the adjacent probes, the connected probe is specific for one of the alleles of a single nucleotide polymorphism. The stuffer sequence contained in the first oligonucleotide probe is preferably indicative of the locus that is to be analysed. The stuffer sequence contained in the second probe is preferably indicative of the nucleotide complementary to the polymorphic site.

To identify the allele of polymorphic site in the target sequence, a pair of oligonucleotide probes can be provided wherein one first probe is provided and one or more second probes (in this case the pair of probes may contain more than two probes). Each second probe then contains a specific nucleotide at the end of the complementary sequence, preferably the 3'-end, in combination with a known length of the stuffer. For instance, in case of an A/C polymorphism, the second probe can contain a specific nucleotide T in combination with a stuffer length of 2 nucleotides and another second probe for this polymorphism combines a specific nucleotide G with a stuffer length of 0. As the primers and the complementary parts of the probes are preferably the same length, this creates a length difference of the resulting amplified connected probes of 2 nucleotides. In case the presence and/or the absence of all four theoretically possible nucleotides of the polymorphic site is desired, the stuffer-specific nucleotide combination can be adapted accordingly. In this embodiment, it can be considered that the locus-specific information is coupled to the length of the stuffer in the first probe and the allele-specific information of the polymorphic site is coupled to the length of the second stuffer. The combined length of the two stuffers can then be seen as indicative of the locus-allele combination. In a sample containing multiple targets sequences, amplified with the same pair of amplification-primers (and hence label) or with multiple pairs of amplifications primers with labels that have overlapping emission spectra, the combined stuffer lengths are chosen such that all connected probes are of a unique length. In a preferred embodiment this principle can be extended to at least ten loci with at least two alleles per locus. A further advantage of using two stuffers, one in each probe, is that by incorporating the majority of the length of the stuffer in the first probe (i.e. the locus-specific probe) the allele-specific probes can remain shorter i.e. the minimum number of bases sufficient for discrimination between the allele specific probes, which saves costs. The incorporation of the complete stuffer sequence in the allele specific probe would require the synthesis of the majority of the stuffer sequence twice.

Detection of Specific Target Sequence

The target sequence contains a known nucleotide sequence derived from a genome. Such a sequence does not necessarily contain a polymorphism, but is for instance specific for a gene, a promoter, an introgression segment or a transgene or contains information regarding a production trait, disease resistance, yield, hybrid vigour, is indicative of tumours or other diseases and/or gene function in humans, animals and plants. To this end, the complementary parts of the first probe and the second probe are designed to correspond to a, preferably unique, target sequence in genome, associated with the desired information. The complementary parts in the target sequence are located adjacent to each other. In case the desired target sequence is present in the sample, the two probes will anneal adjacently and after ligation and amplification can be detected.

Detection of AFLP Markers

AFLP, its application and technology is described in Vos et al., Nucleic Acids Research, vol. 23, (1995), 4407-4414 as well as in EP-A 0 534 858 and U.S. Pat. No. 6,045,994, all incorporated herein by reference. For a further description of AFLP, its advantages, its embodiments, its techniques, enzymes, adapters, primers and further compounds, tools and definitions used, explicit reference is made to the relevant passages of the publications mentioned hereinbefore relating to AFLP. AFLP and its related technology is a powerful DNA fingerprinting technique for the identification of for instance specific genetic markers (so-called AFLP-markers), which can be indicative of the presence of certain genes or genetic traits or can in general be used for comparing DNA, cDNA or RNA samples of known origin or restriction pattern. AFLP-markers are in general associated with the presence of polymorphic sites in a nucleotide sequence to be analysed. Such a polymorphism can be present in the restriction site, in the selective nucleotides, for instance in the form of indels or substitutions or in the rest of the restriction fragment, for instance in the form of indels or substitutions. Once an AFLP marker is identified as such, the polymorphism associated with the AFLP-marker can be identified and probes can be developed for use in the ligation assay of the present invention.

In another aspect the present invention pertains to a nucleic acid probe comprising a part that is capable of hybridising to part of a target sequence, a part that is capable of functioning as a clamp section and preferably further comprising a primer-binding sequence and/or a stuffer. The invention also pertains to a pair of probes, preferably comprising two or more probes wherein each probe comprises a part that is complementary to part of a target sequence and wherein the complementary parts of the probes are located essentially adjacent on the target sequence and wherein each probe further comprises a stuffer, which stuffer is located essentially next to the complementary part and a primer-binding sequence located essentially adjacent to the stuffer and wherein each probe further comprises a clamp section wherein the clamp section is capable of hybridising to a complementary clamp section in at least one of the other probes in the pair of probes.

The invention in a further aspect, pertains to the use of a pair of probes in the analysis of at least one nucleotide sequence and preferably in the detection of a single nucleotide polymorphism, wherein the pair further comprises at least one additional probe that contains a nucleotide that is complementary to the known SNP allele. Preferably the pair comprises a probe for each allele of a specific single nucleotide polymorphism. The use of a pair of probes is further preferred in a method for the high throughput detection of single nucleotide polymorphisms wherein the length of the first stuffer in the first probe is specific for a locus of a single nucleotide polymorphism and the length or the presence of the second stuffer in the second probe is specific for an allele of the single nucleotide polymorphism.

Another aspect of the invention relates to the primers and more in particular to the pair of primers comprising a first primer and one or more second primers, wherein each second primer contains a label and which second primer comprises a nucleotide sequence that is specific for said label.

The present invention also finds embodiments in the form of kits. Kits according to the invention are for instance kits comprising (pairs of) probes suitable for use in the method as well as a kit comprising primers, further a combination kit, comprising primers and probes, preferably all suitably equipped with enzymes buffers etcetera, is provided by the present invention.

The invention also relates to the use of a pair of probes or two or more pairs of probes according to the invention in the detection or determination of the presence or absence of a target sequence in at least one sample.

Section I represents the embodiment wherein one of the probes contains a nucleotide (here represented by A) that is complementary to the nucleotide at the corresponding position in the target sequence (here represented by T). The other probe contains the overhang (E) that contains the nucleotide (here represented by A) at the first unmatched position and wherein the nucleotide at the unmatched position is complementary to the nucleotide in the target sequence to be detected (here represented by T). This will result in the formation of the cleavage structure and subsequent cleavage by the cleavage agent. The resulting cleaved structure can be ligated. Subsequent amplification will provide a set of amplicons that are indicative of the target sequence in the sample.

Section II represents a similar embodiment as section I with the difference that the nucleotide in the probe at the foreseen point of ligation does not match to the target sequence. The nucleotide at the first unmatched position in the overhang does match to the nucleotide in the target sequence. The cleavage structure may be formed and the overhang may be cleaved. However, even if the overhang is cleaved, the two probes will not be ligated as the there is a mismatch in the probes, preventing ligation. Consequently, any amplification will also not be successful.

Section III represents an embodiment wherein the nucleotide at the first unmatched position in the overhang does not match to the nucleotide in the target sequence. The cleavage structure will not be formed and the overhang will not be cleaved. No ligation or amplification will occur.

Figure 5:
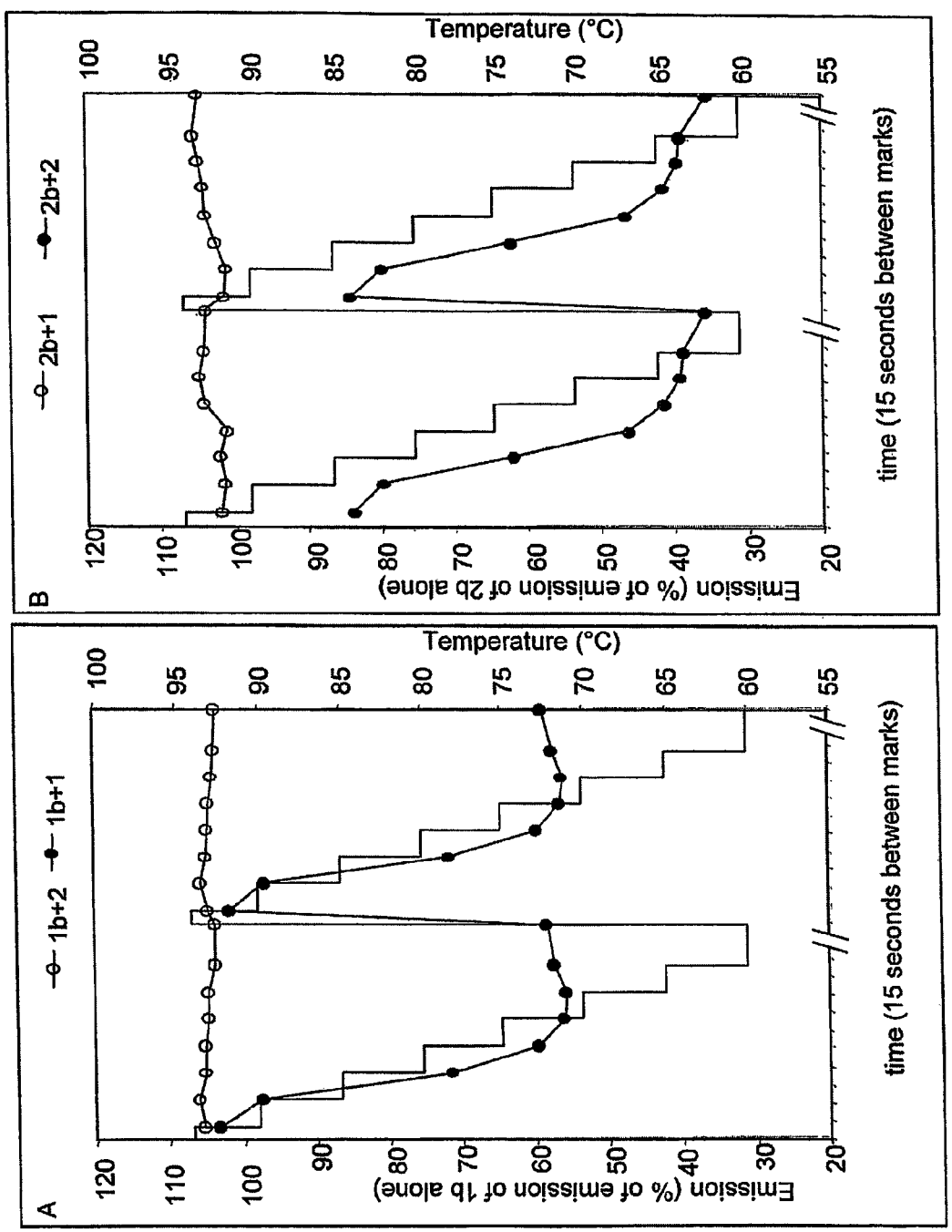

FIG. 5: demonstrates the experiments wherein 5' HEX-labeled allele-specific parts of Keylock probes (1b and 2b) were mixed with 3' Methyl red labeled locus-specific parts of Keylock probes (1 and 2).

Figure 6A:
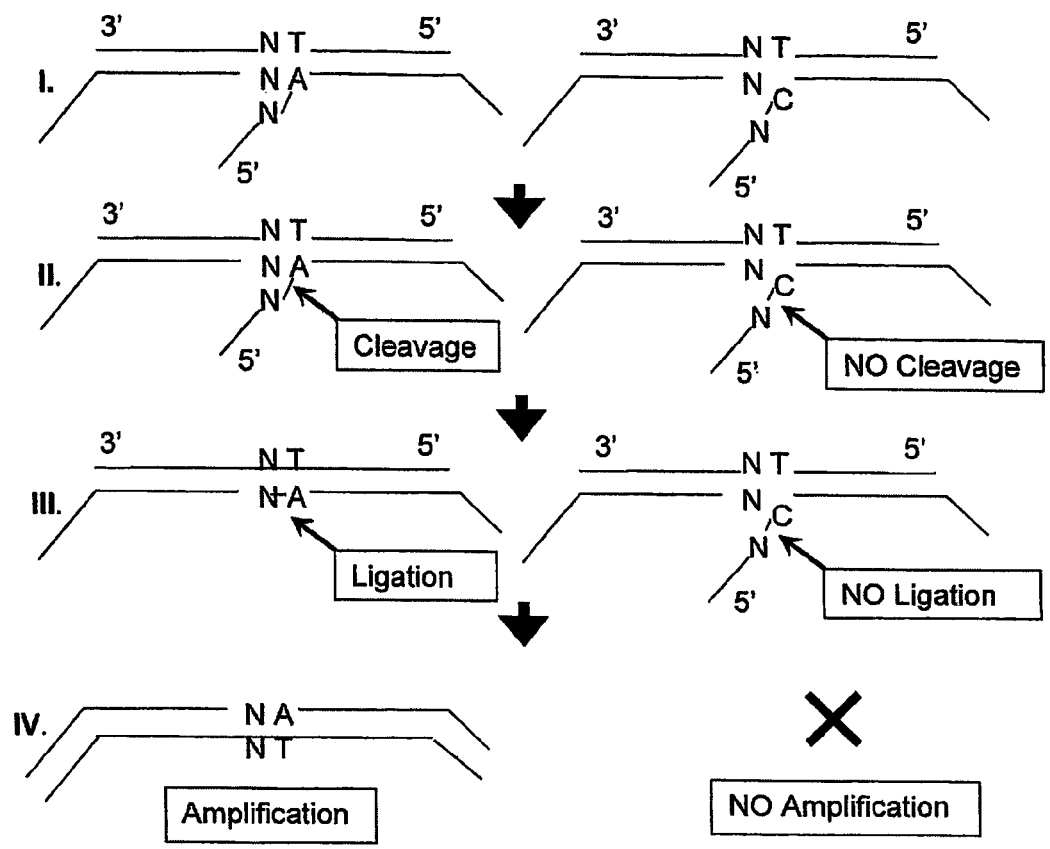

FIG. 6A: Schematic and generalized representation of an SNP-specific or allele-specific oligonucleotide ligation assay wherein the allele-specific nucleotide is provided in the probe that contains the further (extended) region and wherein a cleavage structure is formed with i) the nucleotide in the target sequence that is located adjacent to the SNP to be investigated, ii) the nucleotide of the probe that hybridizes to the nucleotide of i), and iii) the nucleotide of the other probe that is located in the further (extended) region and adjacent to the allele-specific nucleotide in the probe. In this embodiment the cleavage structure is formed adjacent to the SNP. This improves specificity.

Figure 6B:
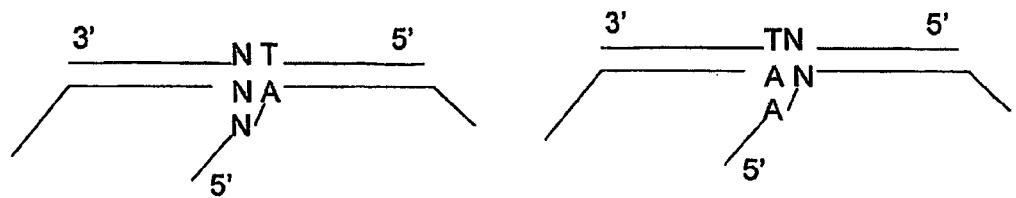

FIG. 6B: schematic representation of two allele specific or SNP-specific oligonucleotide ligation assays, wherein in the first assay the cleavage structure is formed by the nucleotides located adjacent to the SNP to be investigated, depicted as N, and wherein the second assay the cleavage structure is formed by the nucleotides of the SNP to be investigated, depicted as A or T.

Figure 7:
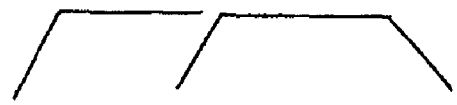
Figure 7:
Figure 7:
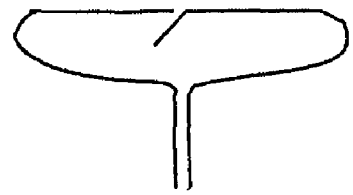

FIG. 7: demonstrates the general applicability of the embodiment of FIGS. 6A and 6B for OLA assays in general, i.e. when using linear probes (1), circularizable/padlock probes (2) and semi-circularizable/Keylock probes (3) of the present invention.

EXAMPLES

Example 1

Description of Biological Materials and DNA Isolation

DNA was isolated from leaf material of 4 homozygous tomato lines using methods known per se, for instance essentially as described in EP 0 534 858, and stored in 1× TE (10 mM Tris-HCl pH 8.0 containing 1 mM EDTA) solution. Concentrations were determined by UV measurements in a spectrophotometer (MERK) using standard procedures, and adjusted to 100 ng/µl using 1× TE.

Example 2

Identification of SNPs

The selected SNPs are identified and summarised in Table 1.

Example 3

Oligonucleotide Padlock Probe Design for Oligonucleotide Ligation Reaction

The circular oligonucleotide padlock probes (5'-3' orientation) were selected to discriminate the SNP alleles for each of the SNP loci described in Example 2. All the probes are phosphorylated at the 5' end. The sequences are summarised in Table 2.

Example 4

Oligonucleotide Keylock Probe Design for Oligonucleotide Ligation Reaction

The linear Keylock probes (5'-3' orientation) were selected to discriminate the SNP alleles for each of the SNP loci described in Example 2. PCR binding regions are underlined, stuffer sequences are double underlined and clamp section are printed in bold. Reverse primers are phosphorylated at the 5' end: p or PH indicates phosphorylated. The sequences are summarised in Table 3.

Example 5

Design of the PCR Amplification Primers

The sequence of one of the primers used for PCR amplification was complementary to the PCR primer binding regions incorporated in the ligation probes described in Examples 3 and 4. The sequence of the second PCR primer matched the PCR primer binding region of the probe. Usually the forward primer is labelled. The concentration of the oligonucleotides was adjusted to 50 ng/µl. The sequence of the primers in 5'-3' orientation are depicted in Table 4.

TABLE 4

PCR amplification primers

| SEQ ID # | Primer nr | | 5'-3' | |
|---|---|---|---|---|
| 61 | MseI+0: | 93E40 | GATGAGTCCTGAGTAA* | M00k |
| 62 | EcoRI+0 | 93L01 | GACTGCGTACCAATTC* | E00k |

*Multiple labels possible

Example 6

Figure 1:
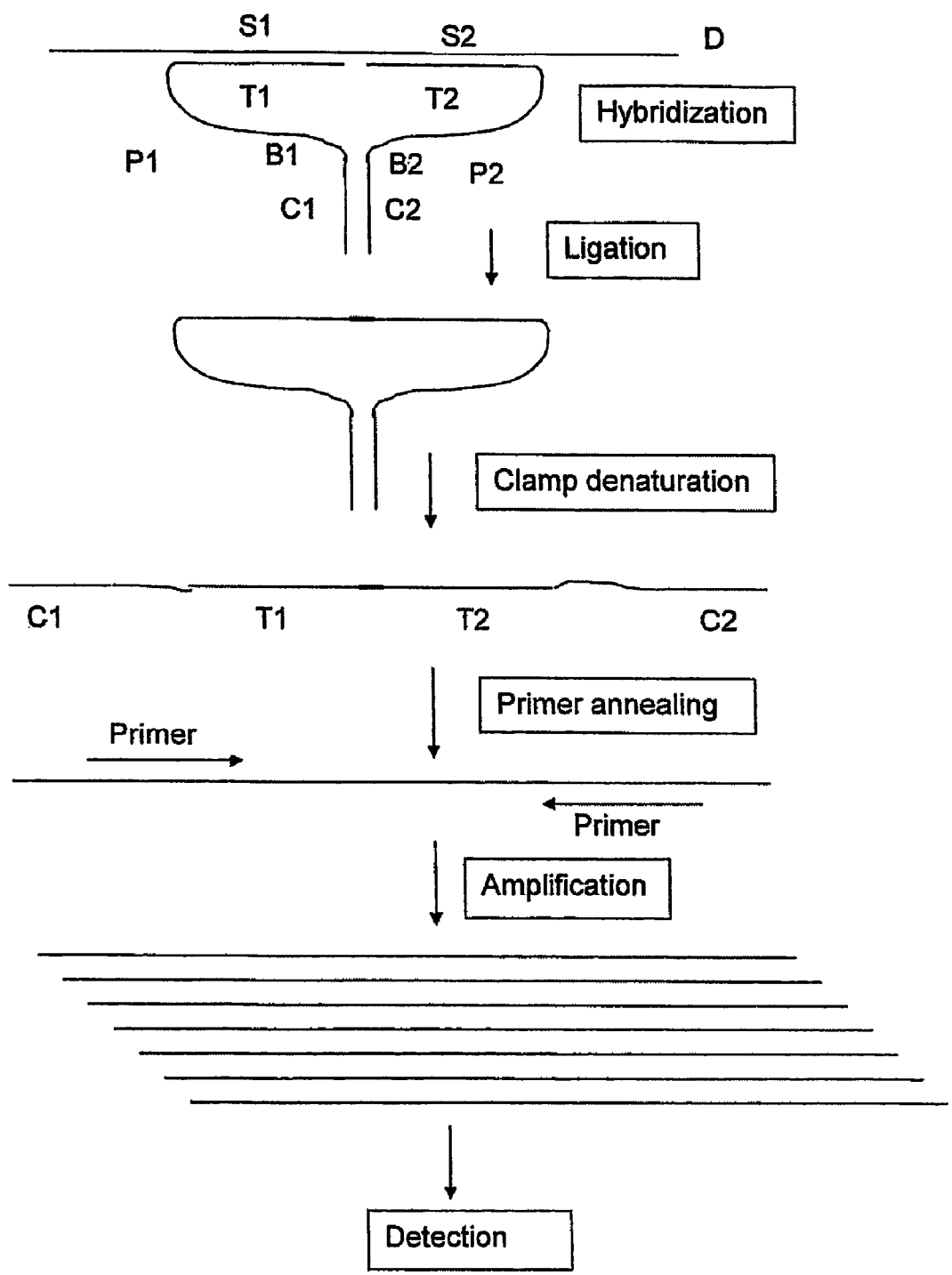
FIG. 1: Schematic representation of structure and functionality of Keylock probes. The probes (P1, P2) each contain a target specific section (T1, T2) complementary to a section (S1, S2) of the target sequence (D). The probes each contain a clamp section (C1, C2) capable of hybridising to each other. The probes each contain a primer binding section (B1, B2) capable of hybridising to a primer. The probes can be hybridised against the target sequence. When the probes are hybridised adjacent on the target sequence, the probes can be ligated together with a ligase. The clamp may be denatured after which primers can be annealed to the connected probes and the connected probes can be amplified or multiplied, for instance using PCR or another suitable amplification technique. After amplification, the ligated and amplified probes can be detected.
Figure 2:
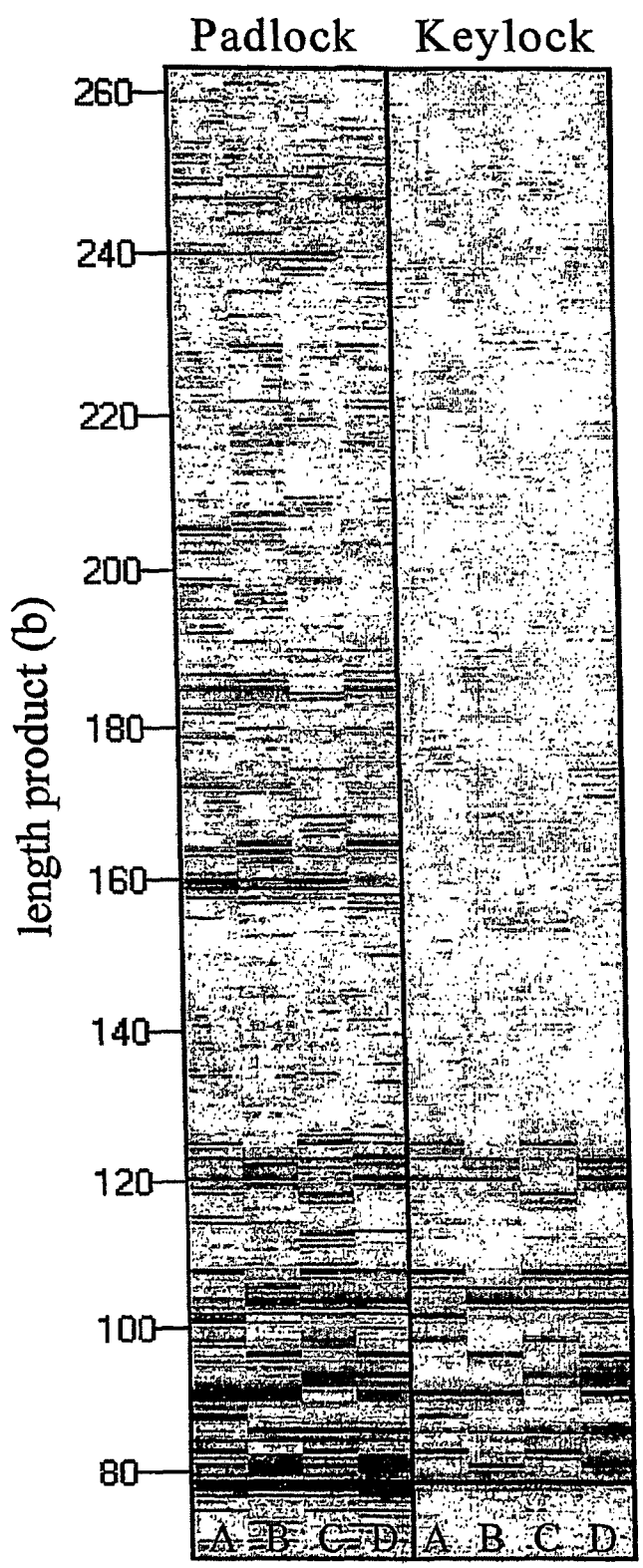
FIG. 2: Comparison between padlock and Keylock assays. Tomato lines A, B, C, and D were assayed with a 10-plex pair of padlock-probes and a 10-plex pair of Keylock-probes, designed on the same loci. All ligations contained 100 ng genomic DNA. For padlock-assays 0.5 fmol of each probe was used, for Keylock assays 0.5 fmol of each allele-specific probe and 1 fmol of each locus-specific probe were used. The image of the MegaBACE traces was generated with SNPXtractor software (Keygene N.V.), which converts electropherograms into pseudo-gel images.

Ligation and Amplification 4 samples (samples 1-4) of homozygous tomato lines (Example 1) were subjected to a multiplex oligonucleotide ligation reaction using a mixture of 20 padlock probes (2 probes per locus or 30 Keylock probes (3 probes per locus). Conditions used were 1× Taq DNA ligase buffer (NEB), 0.2 U/µl Taq DNA ligase, and 0.05 fmol/µl of each probe in a volume of 10 µl. Ligation was performed in a thermocycler (Perkin Elmer) with the following cycling conditions: 2 minutes at 94° C.+10*(15 seconds at 94° C.+60 minutes at 60° C.)+4° C. continuously. Following ligation, the 10 µl ligation product was diluted with 30 µl 1× Taq DNA ligase buffer. Ten µl of the diluted ligation reactions was used to perform a PCR using a labelled E00k primer combined with M00k. The E00k primer was labelled with JOE to enable detection on the MegaBACE. Conditions used in the PCR were 30 ng labelled E00k primer and 30 ng M00k primer, 1× Accuprime buffer I, 0.4 ul Accuprime polymerase (Invitrogen) on 10 µl diluted ligation product in a 20 µl PCR reaction. PCR was performed in a thermocycler with the following cycling conditions: 2 minutes at 94° C.+35*(15 seconds at 94° C.+30 seconds at 56° C.+60 seconds at 68° C.)+4° C. continuously. PCR product was purified using Sephadex 50 and diluted 80 times with MQ. Diluted PCR product was analysed on the MegaBACE. The results are presented in FIG. 2

Buffer Compositions:

1× Tag DNA Ligase Buffer 20 mM Tris-HCl 25 mM potassium acetate 10 mM Magnesium acetate 10 mM DTT 1 mM NAD 0.1% Triton X-100

(pH 7.6@25° C.)

1×AccuPrime Tag DNA Polymerase Buffer 20 mM Tris-HCl (pH8.4)

50 mM KCl 1.5 mM MgCl$_2$ 0.2 mM dGTP, dATP, dTTP and dCTP thermostable AccuPrime™ protein 10% glycerol.

Example 7

Purification and Dilution of Amplified Connected Probes

In case of detection using the MegaBACE 1000 capillary sequencing instrument, desalting and purification of the PCR reactions mixtures was carried in 96-well format, using the following procedure:

A. Preparation of the 96-Well Sephadex Purification Plates

Dry Sephadex™ G-50 superfine (Amersham Pharmacia Biotech, Uppsala, Sweden) was loaded into the wells of a 96-well plate (MultiScreen®-HV, Millipore Corporation, Bedford, Mass., USA), using the 45 microliter column loader (Millipore Corporation) as follows:
 a) Sephadex G-50 superfine was added to the column loader.
 b) Excess Sephadex was removed from the top of the column loader with a scraper.
 c) The Multiscreen-HV plate was placed upside-down on top of the Column Loader.
 d) The Multiscreen-HV plate and the Column Loader were both inverted.
 e) The Sephadex G-50 was released by tapping on top or at the side of the Column Loader.
 f) Next, the Sephadex G-50 was swollen en rinsed as follows:
 g) 200 µl Milli-Q water was added per well using a multichannel pipettor.
 h) A centrifuge alignment frame was placed on top of a standard 96-well microplate, the Multiscreen-HV plate was place on top and the minicolumns were packed by centrifugation for 5 min at 900 g.
 i) The 96-well plate was emptied and placed back.
 j) Steps 5-7 were repeated once.
 k) 200 µl Milli-Q water was added to each well to swell the Sephadex G-50 and incubated for 2-3 hours. Occasionaly, at this stage the Multiscreen-HV plates with swollen mini-columns of Sephadex G-50 superfine were tightly sealed with parafilm and stored a refrigerator at 4° C. until further use.
 l) A centrifuge alignment frame was placed on top of a standard 96-well microplate, the Multiscreen-HV plate was placed on top of the assembly and the minicolumns were packed by centrifugation for 5 min at 900 g.
 m) The 96-well microplate was removed.
 n) The mixtures containing the amplified connected probes were carefully added to the centre of each well.
 o) Using the centrifuge alignment frame, the Multiscreen-HV plate was placed on top of a new standard U-bottom microtitre plate and centrifugation was carried out for 5 min at 900 g.
 p) The eluate in the standard 96-well plate (approximately 25 µl per well) contains the purified product.

B. Dilution of the Purified Products

Purified samples were diluted 25-75 fold in Milli-Q water before injection.

Example 8

Capillary Electrophoresis on the MegaBACE

Preparation of the Samples:

A 800-fold dilution of ET-900 Rox size standard (Amersham Biosciences) was made in water. 8 µl diluted ET-900 Rox was added to 2 µl purified sample. Prior to running, the sample containing the sizing standard was heat denatured by incubation for 1 min at 94° C. and subsequently put on ice.

Detection on the MegaBACE:

MegaBACE capillaries were filled with 1× LPA matrix (Amersham Biosciences, Piscataway, N.J., USA) according to the manufacturer's instructions. Parameters for electrokinetic injection of the samples were as follows: 45 sec at 3 kV. The run parameters were 110 min at 10 kV. Post-running, the cross-talk correction, smoothing of the peaks and cross-talk correction was carried out using Genetic Profiler software, version 1.0 build 20001017 (Molecular Dynamics, Sunnyvale, Calif., USA), and electropherograms generated.

Example 9

Functionality and Specificity of Clamp Sections of Keylock Probes

Linear Keylock probes (5-'3') containing fluorescent groups at the ends containing the clamp sequence were designed for SNP loci 34 and 39 described in Example 2, to demonstrate experimentally that the specific formation of locked clamps, based on the occurrence of FRET (fluorescence resonance energy transfer), which can be recorded by a real-time PCR apparatus. The rationale behind this approach is that FRET occurs when the donor and acceptor fluorophores attached to the respective clamp sections of the forward and reverse Keylock probes are in close proximity when the clamp is formed, resulting in FRET from the donor to the acceptor fluorophore which is recorded.

Conversely, when the Keylock probes are not bound at their respective clamp sections, no such energy transfer occurs and no (or a lower) fluorescent signal is observed from the acceptor dye.

The fluorophore-labeled forward probe of SNP locus 34 is labeled with Methyl Red at its 3' end. {SEQ ID 67}. This probe is referred to as Keylock FRET probe 1. The reverse Keylock probe (of the A allele) of SNP locus 34 is labeled with HEX at its 5' end. {SEQ ID 63}. This probe is referred to as Keylock FRET probe 1A.

The reverse Keylock probe (of the G allele) of SNP locus 34 is labeled with HEX at its 5' end. {SEQ ID 64}. This probe is referred to as Keylock FRET probe 1B. The fluorophore-labeled forward probe of SNP locus 39 is labeled with Methyl Red at its 3' end. {SEQ ID 68}. This probe is referred to as Keylock FRET probe 2. The reverse Keylock probe (of the T allele) of SNP locus 39 is labeled with HEX at its 5' end. {SEQ ID 65}. This probe is referred to as Keylock FRET probe 2A.

The reverse Keylock probe (of the G allele) of SNP locus 39 is labeled with HEX at its 5' end. {SEQ ID 66}. This probe is referred to as Keylock FRET probe 2B.

The following probes have been used:

| SEQ ID # | Locus | Probe no | Length (bp) | 5' HEX |
|---|---|---|---|---|
| 63 | 34 | 03F481(1A) | 67 | GCCGGCGGGCCCGGCCGGCG<u>GA</u><br><u>TGAGTCCTGAGTAACGC</u>CTTCA<br>TATTGATGGTTTTGTTTTTGTT<br>A |
| 64 | 34 | 03F482(1B) | 65 | GCCGGCGGGCCCGGCCGGCG<u>GA</u><br><u>TGAGTCCTGAGTAACG</u>TTCATA<br>TTGATGGTTTTGTTTTTGTT<i>G</i> |

-continued

| 65 | 39 | 03F483(2A) | 64 | GGCGCGCGGCCCGCGCGCCGGA TGAGTCCTGAGTAACGCTGTTG TTCCTTGTTGCATCTCCTTT |
| 66 | 39 | 03F484(2B) | 62 | GGCGCGCGGCCCGCGCGCCGGA TGAGTCCTGAGTAACGGTTGTT CCTTGTTGCATCTCCTTG |

| SEQ ID # | LocusPrimer no | Length (bp) | 5' PH; 3' Methyl red |
|---|---|---|---|
| 67 | 34 03G464(1) | 82 | ACGCTTCTTCCTTGTTGAGAGG GGATGCTCAGGCTATCGACATG GGGAATTGGTACGCAGTCCGCC GGCCGGGCCCGCCGGC |
| 68 | 39 03G465(2) | 60 | TCACAAGCTCCCATCGCATCAT GGGAATTGGTACGCAGTCCGGC GCGCGGGCCGCGCGCC |

Mixing of equimolar amounts of Keylock FRET probes (1 and 1A) or (1 and 1B) and subjecting them to the hybridisation conditions described in Example 6 allows monitoring whether hybridisation of the clamps takes place, and if so, at which temperature.

Similarly, mixing of equimolar amounts of Keylock FRET probes (2 and 2A) or (2 and 2B) and subjecting them to the hybridisation conditions described in Example 6 allows monitoring whether hybridisation of the clamps takes place, and if so, at which temperature.

Conversely, mixing of equimolar amounts of Keylock FRET probes 1+2A or 1+2B is not expected to yield a specific Keylock probe for either locus 34 or 39, because no specific hybridisation of their clamp sections is expected to take place. The same applies to the combination of Keylock FRET probes 2+1A or 2+1B when they are mixed in equimolar amounts and subjected to the hybridisation conditions described in Example 6.

Figure 3:
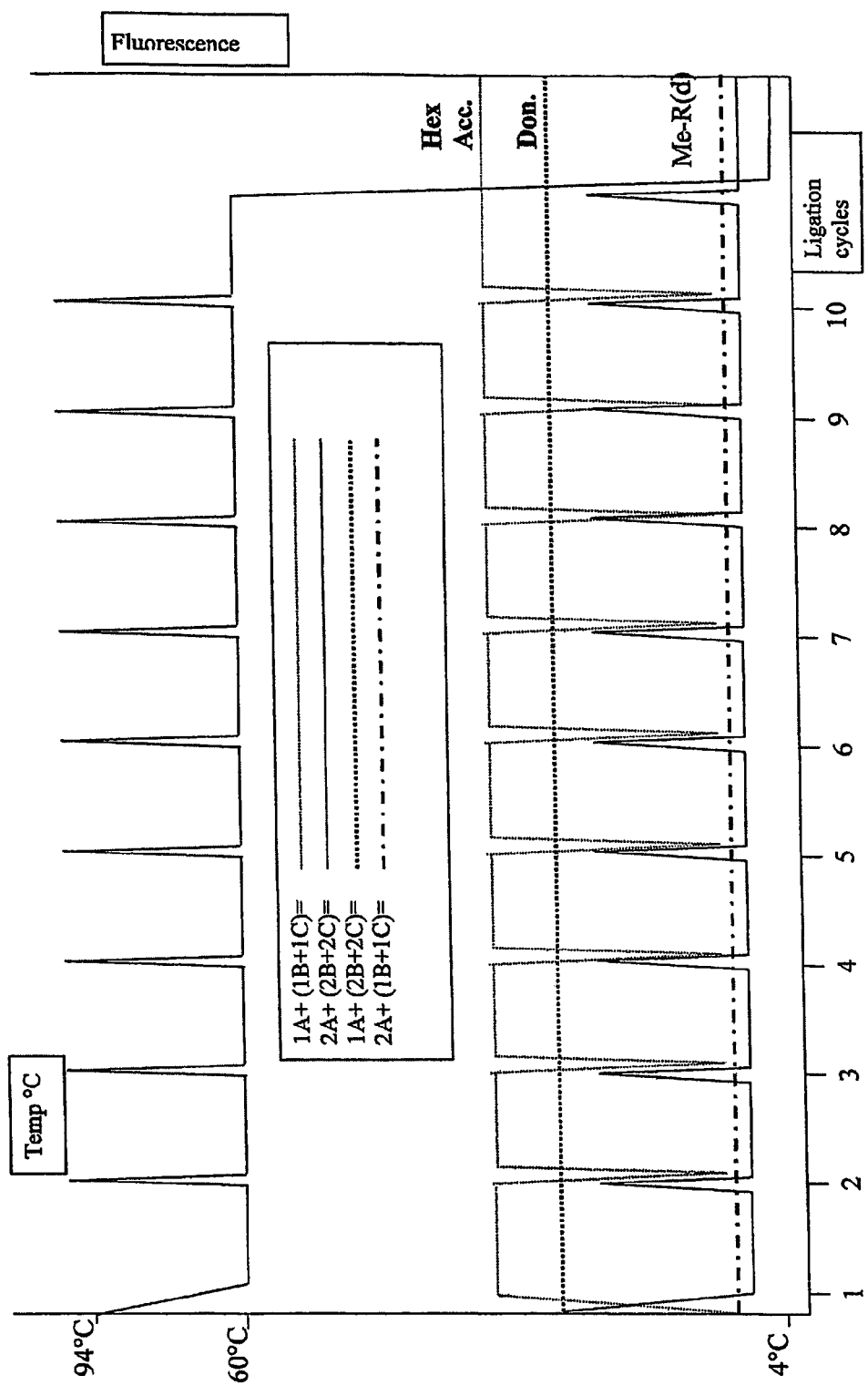
FIG. 3: Representation of fluorescence intensity profiles of Keylock FRET Probes. Profile: 2 min 94° C.+10*(15 sec 94° C., 60 min 60° C.)+4 min cont. Clamp formation is observed at about 75° C.
Figure 4:
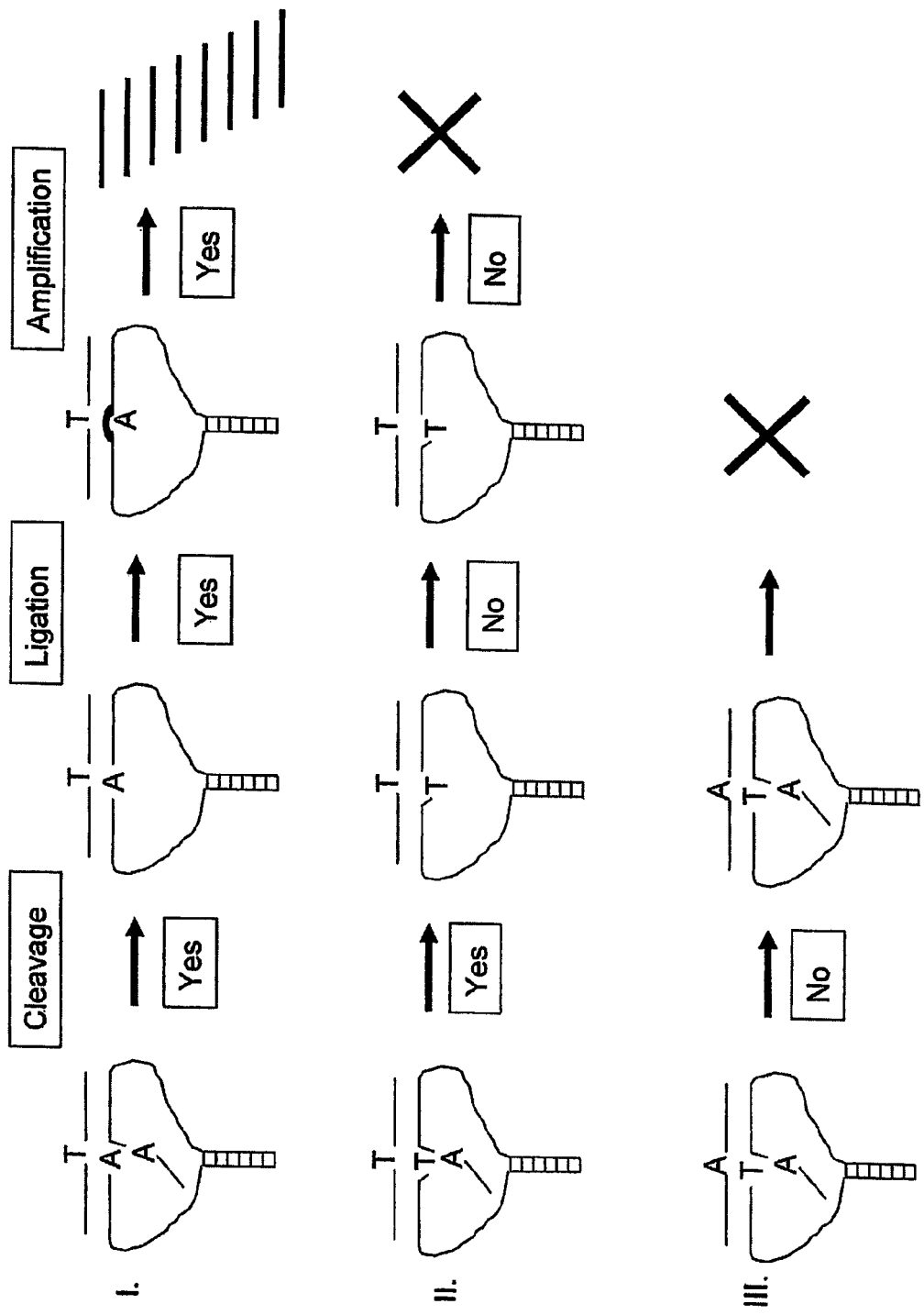
FIG. 4: Schematic and generalized representation of an oligonucleotide ligation assay (based on the probes of the invention) wherein, when a first probe and a second probe are annealed to the target sequence, one of the probes contains an overhang and/or overlap (E) at the foreseen point of ligation. The overhang can be removed using an enzyme that cleaves these cleavage structures in highly specific manner after which ligation, amplification and detection can proceed in the conventional manner.

FIG. 3 shows the expected fluorescence intensity profiles of the acceptor fluorophore HEX that is expected for the above-mentioned combinations of probes, which consists of 2 cycles of repeated denaturation and hybridisation.

The experiment has been performed according to the conditions described in Example 6, with the sole exception that the concentration of the forward and reverse Keylock probes was increased to 1.0 pmol/μl instead of 0.05 fmol/μl in order to meet the detection sensitivity requirements of the detector, the ABI PRISM 7700 real-time detector. Although this concentration difference may influence the efficiency of the clamp hybridization, it is not likely that it affects its specificity, nor the temperature at which clamp formation occurs.

FIG. 5 demonstrates the experiments wherein 5' HEX-labeled allele-specific parts of Keylock probes (1b and 2b) were mixed with 3' Methyl red labeled locus-specific parts of Keylock probes (1 and 2). If a clamp is formed, Methyl red comes into close proximity of the HEX label and quenches its emission at 556 nm. Clamps should be formed between 1b and 1 and between 2b and 2, and not between 1b and 2 or 2b and 1. HEX emission was measured in 50 μl of 1 μM oligo solution, with the ABI PRISM™ 7700 Sequence Detector, using the raw signal in wavelength bin 11 at the end of each temperature step. The emission is represented as percentage of the emission obtained when measuring the HEX labeled oligo separately, in the last two cycles of the following profile: 2' 94° C.; 10*[15"94° C.; 60' 60° C.]; 11*[15" 94° C.; 30" 90° C.; 30" 85° C.; 30" 80° C.; 30" 75° C.; 30" 70° C.; 30" 65° C.; 15" to 50'15"(5' increase each cycle) 60° C.] followed by hold at 25° C.

FIG. 5 clearly demonstrates the specificity of clamp formation of the matching probe pairs 1+1B (FIG. 5A) and 2+2B (FIG. 5B), but not between non-matching probe pairs 1B+2 (FIG. 5A) or 2B+1 (FIG. 5B). In addition, in FIG. 5 is shown that clamp formation starts taking place at around 90° C., which in line with the high melting temperature of the clamps, and is complete in at around 70-75° C. in the thermocycling process.

Example 10

Comparison of Padlock and Keylock Probes

In order to compare the performance of Keylock probes in ligation assays to that of padlock-probes, 4 different SNPs (A, B, C, D) were selected and for each a padlock probe and a Keylock probe was designed. The Keylock-probes were ordered from the same company as the padlock probes (Metabion). A selection of well known SNPs derived from 4 tomato lines was made so that for each allele at least one positive score would be obtained. The results obtained with 100 ng of genomic DNA and 0.5 fmol of each allele-specific probe are given in FIG. 2. The formation of concatamers when padlock probes are used are clearly visible at 160 and 240 bp (concatamers of padlock probe length 80). The concatamers are absent when the Keylock probes are used.

Example 11

Keylock Probes using Cleavase Approach.

To demonstrate the feasibility of the cleavase-ligation approach, the reverse probes from Table 3, (Keylock no: 02W661, 02W662, 02W663, 02W664, 02W665, 02W666, 02W667, 02W668, 02W669, 02W670) were extended at their 5' end with a further region having the sequence 'CACAC'. The extended probes were combined with the forward probes of Table 3 and subjected to a hybridization and ligation protocol wherein the enzymes (both ligase and Cleavase (obtained from Third Wave Inc. and used 'as is' in amounts varying between 1 and 10 microliter)) are added. The resulting mixture is incubated in a thermocycler (Perkin Elmer) with the following cycling conditions: 4 minutes at 94° C.+240 minutes at 60° C.+4° C. continuously. Subsequently, the mixture is amplified under the conditions as described in Example 6. The expected products were found, i.e. ligated probes with lengths corresponding to the results obtained with the reverse probes of Table 3 that were not extended, indicating that the cleavase step and the ligations step were successful, indicating that the method works. Experiments were performed in absence of (combinations of) enzymes. These experiments demonstrated that both enzymes are necessary for this probe type to come to a ligated probe.

TABLE 1

Selected SNP sequences and position of the SNP.

| SEQ ID # | Set 4 code | Fragment | Locus nr. | Length | SNP pos. | SEQUENCE |
|---|---|---|---|---|---|---|
| 1 | 95 | 43F | 31 | 472 | 246 | TATCCACTCAGGTCTC-CGC AAGCCAGAAATGGGATAT |

TABLE 1-continued

Selected SNP sequences and position of the SNP.

| SEQ ID # | Set 4 | Fragment code | Locus nr. | Length | SNP pos. | SEQUENCE |
|---|---|---|---|---|---|---|
| | | | | | | ACACCTTGTTACGACCYT CAAGCCATCCACTACTGC AATCTGTCATGTCACAGA TGTTCGGAAGATAATGTA TAAGTACAACTATATAGT CGGAWTTGCATCTAGTCT AGCATTCGGAAAATGGAA GCCATGCTACTTCTAGCA TAAAAAACAGCAGCTAGA AATCGTAACTCCAATGAT ACGAGGAAGTATTCAGAG TTTAGAGTGAWGTACAAT GCAATTTAGAGAACAAGC ATCTGCACATCRAAGTTA CCTAGGTCCTCAGCGCCT GATGGACTTCCAACTTGT TCAAGAAGGCGATAAAGG TCTTTCTCATTGAATCCT TCAGGTGGAGAGTAGTTT TCACAAACTGCAAATGCC TCTGCACAGCGGAAAGAT TGAATTAGATTTATGTTA TATAGCCATTCTAGTCTT GCTTTAATGGATCTTTCT CGA |
| 2 | 96 | 61F | 32 | 222 | 175 | CCACAGTTTCATGCTGCA CCTACATGTGTAAGCAAC TATCATAGCAAGTCTCGG AACAATTGGTAGGAAAAA ATCMYKTAAGGATATGAA ACATACTGTYCTTTCTTC ATCTGAGTCTGYAGAGTT AATTTTTAACTCTTGGGA TAAATGCAAAGAWTTAGA CATGGAKGAGTYCTTAAC ACGTCCAGACAAGAGGCG TAACACAGGTACACCTTT TCTCGA |
| 3 | 97 | 64F | 33 | 133 | 121 | TTGTGCTTGATGAATTGT AGGTCCAGTGCAGGTTTG CTTCTAAAACAGGGAGCA CTTTGCAAGTGGTGAAAG TTCTATTAGCTGGGAAAG TGTAGTTTGAGCAGTTTT GAGCTGARTTAACAAGAA AAATCGA |
| 4 | 98 | 75F | 34 | 250 | 47 | CCGCCACTGGGTAATTGA GTTTCATATTGATGGTTT TGTTTTTGTTRACGCTTC TTCCTTGTTGAGAGGGTT CAATGGAGAGATTCTATC TCGTCCTCCATTAGTTGA AGCTATTGCCTTTGATCC TATCCTTTCAAAGGYCAA GATGATTGCAGATAATTG GAATCCATTAACCAATGA TTCTACGGAAAATTTATT CCCTCACTGGAGGAGATG GGCAGAGATAAATATGAG ATTTTGTGATGACAT |
| 5 | 99 | 92R | 35 | 284 | 84 | TCGAGTAAGGCGGATGGA TATGGAACAAGCCATTTC AAGGAGCAATTTCCCAGG ATTTTCAGCTTTGCAACA GCAGAAGTGTAYCTCTGC AGAGATAGATCATAACCT TTGGAAAGGTGTAGTAAT TGTCAAAGGGAGGAATGA GCCAGGAAACTGATAGAC TATGTTGCGAAAATAAGC TATACTTCACTAAAAAAA GGCTAGACGTTTGAGAAA TGAAGCAAGAACTAACAC CTCTCACCAATTGCATCA TTTTCTTAGTTCAGTTGA TGTGATGAGCTTGT |
| 6 | 100 | 28R | 36 | 320 | 31 | TCGATATCCWCTCTTGTT TGTTGCAGGAGCWGAACT ATAAATTGCTTGCAGGAA CCTTGACATATGCTTTCT GTTGAGACTTGAATCACC AGCATGGATTTGAATGCC TTGCCACAGCCAGAGGAT GACGAYGAGATTTTTGGA CAACAATTAGAAGATGAA CCACAAGAACCTATTTTA CGTAGTGATGAGCSTGCA GATTATGTCACGAGTGCT GTAGAGATTTCACGTCGC GTATGTTTCTGCTTATAC TGCTCGCTGTATCAACTA TTGAACYGTACTACTACT TGARCTTGCTCGTTTATT GGATATTTCTTTTT |
| 7 | 101 | 14446E10 | 40 | 193 | 159 | GAATTCACACTASGTTCG ATGAAATTGAAACGTTCT CTTTCTGAAGAAKATACA CAAGAAAAAATCTTATAG TCCTCAACAATATTCTTC TTCGTAACAGAAACACG GAAGAAAATCTCTTCTGA AAATCCCTATAATCACTG GCTGGAACTTCTCCSAAC TCTCAATTTTTCAACCTT CTCTATGTTAA |
| 8 | 102 | 14447C06 | 38 | 291 | 89 | CTGCAGAADTACTGTTTG TTCAGGACTTACTAAATA TCCTAAACAAAATTGATG ATAGAGCCAATAATGTAT GCATGATTGGCGGTCCRT TCTTTTGTTATAGCAAGA GCTTGAAGCTAATTTTGT TTGTCATAATGGCCGCAC TAATTGTTTATTATCTCA GAATGAACAAAAAGAAGC AAGTCAGAAGCTTTSTAC TCTATACTGAACAACTTT GGAATTGGAACTATGTAC TTATCTAGCCACGCCTCA TAGATCTTTGTGGTTTAG GAGTGTTAA |
| 9 | 103 | 14446E01 | 39 | 337 | 122 | GAATTCACAATGAAAAAK GKDGTAAAAACACGAAAT CAATCAAGCATGCAAGAG ATAATGTTGTCCATCCAG TTGTTGTTGATGTTTCGG TATTGTATGTGTGTTGGG AGGAGTTATCTGGRCAGC AAGTCGAGGTTTGAACGT CAAAAAGGTATGGGTTGT CTTCTCTCTTTTGTCCCTT TTCGAAGAGACCCCTAAG GTTCAGACGAATCTATTC CAAAAACTAGGGTTGTTC CTTGTTGCATCTCCTTKT CACAAGCTCCCATCGCAT CATAAGTAGGGTATGTTT GATGGTAGAATTTACGGA |

TABLE 1-continued

Selected SNP sequences and position of the SNP.

| SEQ ID # | Set 4 | Fragment code | Locus nr. | Length | SNP pos. | SEQUENCE |
|---|---|---|---|---|---|---|
| | | | | | | TGTAATTTACTTTTGAAA TGATTATGTTAA |
| 10 | | 10414157A04 | 37 | 373 | 63 | AGAGAGACGAGAGCTCGA CTAGTGATAGTGTTATGT GCAACAGTTGAATAGAAA GATGYACACGAGCCTCGG ATCAATGGCAGGGAAAGA GGCGTGGTGCTACGAACC ATAAAGGCAAGGTTGAGC TTTCCTTTACAGAGTACA TCGCCTATTCCATACTCC GCTGATACTCTTTGATAA ATCAAAATCTGTGGTGAT CTCGTAGTTCTTGGGGAT CCCAGCCAAAACCACCTT CGAGGTTCAACACAACAT AGACAGTATGGCAGAATA TCAAGACAATGACTGCTC GAAACTGCTGATGGCATT ATGTGCAACCGTTGAATA GAGAGATGTACACGAGTC TCGGATCAATGGCAGGAA AAGAGAGTGCTTG |

W = A or T; M = A or C; R = A or G; Y = C or T; K = G or T; S = G or C; H = A, C or T; B = C, G or T; V = A, C or G; D = A, G or T; N = A, C, G or T

TABLE 2

Oligonucleotide padlock probes for detection of SNPs from Table 1.

| SEQ ID # | Padlock nr. | Fragment code | Locus nr. | Length (bp) | 5'-PH-3' |
|---|---|---|---|---|---|
| 11 | 02W601 | 43F | 31 | 124 | GTACAATGCAATTTAGAGA ACAAGCGGgAATTGGTACG CAGTCGATGAGTCCTGAGT AACGCTGATCCGATCGATA TCGACGTAGCTGCATCGTA ATCGGGAAGTATTCAGAGT TTAGAGTGAA |
| 12 | 02W602 | 43F | 31 | 122 | GTACAATGCAATTTAGAGA ACAAGCGGGAATTGGTACG CAGTCGATGAGTCCTGAGT AACGCATCCGATCGATATC GACGTAGCTGCATCGTAAT CGGGAAGTATTCAGAGTTT AGAGTGAT |
| 13 | 02W603 | 61F | 32 | 119 | CTTAACACGTCCAGACAAG AGGCGGGAATTGGTACGCA GTCGATGAGTCCTGAGTAA CGCACCATGTCGACGTAGA TCCGTATAGCACTGAGTCG CAAAGAATTAGACATGGAT GAGTT |
| 14 | 02W604 | 61F | 32 | 117 | CTTAACACGTCCAGACAAG AGGCGGGAATTGGTACGCA GTCGATGAGTCCTGAGTAA CGCCCATGTCGACGTAGAT CCGTATAGCACTGAGTCCA AAGATTTAGACATGGAGGA GTC |

TABLE 2-continued

Oligonucleotide padlock probes for detection of SNPs from Table 1.

| SEQ ID # | Padlock nr. | Fragment code | Locus nr. | Length (bp) | 5'-PH-3' |
|---|---|---|---|---|---|
| 15 | 02W605 | 64F | 33 | 114 | TTAACAAGAAAAATCGGTC AGGACTGGGAATTGGTACG CAGTCGATGAGTCCTGAGT AACGCCGTACGCATGCTAA CGTTACGGACTATCTAGTT TGAGCAGTTTTGAGCTGAA |
| 16 | 02W606 | 64F | 33 | 112 | TTAACAAGAAAAATCGGTC AGGACTGGGAATTGGTACG CAGTCGATGAGTCCTGAGT AACGCTACGCATGCTAACG TTACGGACTATCTAGTTTG AGCAGTTTTGAGCTGAG |
| 17 | 02W607 | 75F | 34 | 109 | ACGCTTCTTCCTTGTTGAG AGGGGGGAATTGGTACGCA GTCGATGAGTCCTGAGTAA CGCCGATGCTCAGGCTATC GACATGTTCATATTGATGG TTTTGTTTTGTTA |
| 18 | 02W608 | 75F | 34 | 107 | ACGCTTCTTCCTTGTTGAG AGGGGGGAATTGGTACGCA GTCGATGAGTCCTGAGTAA CGCATGCTCAGGCTATCGA CATGTTCATATTGATGGTT TTGTTTTGTTG |
| 19 | 02W609 | 92R | 35 | 104 | CTCTGCAGAGATAGATCAT AACCTGGGAATTGGTACGC AGTCGATGAGTCCTGAGTA ACGCATCACGTCATGCTGA GCATAGCTTTGCAACAGCA GAAGTGTAT |
| 20 | 02W610 | 92R | 35 | 102 | CTCTGCAGAGATAGATCAT AACCTGGGAATTGGTACGC AGTCGATGAGTCCTGAGTA ACGCCACGTCATGCTGAGC ATAGCTTTGCAACAGCAGA AGTGTAC |
| 21 | 02W611 | 28R | 36 | 99 | GAACTATAAATTGCTTGCA GGAACCGGGAATTGGTACG CAGTCGATGAGTCCTGAGT AACGCTCGCTAACGTTACG CTCTCTTGTTTGTTGCAGG AGCA |
| 22 | 02W612 | 28R | 36 | 97 | GAACTATAAATTGCTTGCA GGAACCGGGAATTGGTACG CAGTCGATGAGTCCTGAGT AACGCGCTAACGTTACGCA CTCTTGTTTGTTGCAGGAG CT |
| 23 | 02W613 | 14446E10 | 40 | 94 | AACTCTCAATTTTTCAACC TTCTCTAGGGAATTGGTAC GCAGTCGATGAGTCCTGAG TAACGCGTCATTCGAATCA CTGGCTGGAACTTCTCCC |
| 24 | 02W614 | 14446E10 | 40 | 92 | AACTCTCAATTTTTCAACC TTCTCTAGGGAATTGGTAC GCAGTCGATGAGTCCTGAG TAACGCCATTCGAATCACT GGCTGGAACTTCTCCG |

TABLE 2-continued

Oligonucleotide padlock probes for detection of SNPs from Table 1.

| SEQ ID # | Padlock nr. | Fragment code | Locus nr. | Length (bp) | 5'-PH-3' |
|---|---|---|---|---|---|
| 25 | 02W615 | 14447C06 | 38 | 89 | TTCTTTTGTTATAGCAAGAGCTTGAAGGGAATTGGTACGCAGTCGATGAGTCCTGAGTAACGCCCGATGTATGCATGATTGGCGGTCCA |
| 26 | 02W616 | 14447C06 | 38 | 87 | TTCTTTTGTTATAGCAAGAGCTTGAAGGGAATTGGTACGCAGTCGATGAGTCCTGAGTAACGCCATGTATGCATGATTGGCGGTCCG |
| 27 | 02W617 | 14446E01 | 39 | 84 | TCACAAGCTCCCATCGCATCATGGGAATTGGTACGCAGTCGATGAGTCCTGAGTAACGCTGTTGTTCCTTGTTGCATCTCCTTT |
| 28 | 02W618 | 14446E01 | 39 | 82 | TCACAAGCTCCCATCGCATCATGGGAATTGGTACGCAGTCGATGAGTCCTGAGTAACGGTTGTTCCTTGTTGCATCTCCTTG |
| 29 | 02W619 | 14157A04 | 37 | 79 | ACACGAGCCTCGGATCAATGGGAATTGGTACGCAGTCGATGAGTCCTGAGTAACGTGCAACAGTTGAATAGAAAGATGT |
| 30 | 02W620 | 14157A04 | 37 | 77 | ACACGAGCCTCGGATCAATGGGAATTGGTACGCAGTCGATGAGTCCTGAGTAACGCAACAGTTGAATAGAAAGATGC |

TABLE 3

Oligonucleotide Keylock probes for detection of SNPs from Table 1.

| SEQ ID # | Keylock nr. | Fragment code | Locus nr. | Length (bp) | 5'-PH-3' sequence |
|---|---|---|---|---|---|
| 31 | 02W641 | 43F | 31 | 124 | GCCGCGCCCGGGCCGCCCGGGATGAGTCCTGAGTAACGCTGGAAGTATTCAGAGTTTAGAGTGAA |
| 32 | 02W642 | 43F | 31 | 122 | GCCGCGCCCGGGCCGCCCGGGATGAGTCCTGAGTAACGGGAAGTATTCAGAGTTTAGAGTGAT |
| 33 | 02W661 | 43F | 31 | rev | GTACAATGCAATTTAGAGAACAAGCGATCCGATCGATATCGACGTAGCTGCATCGTAATCGGGGAATTGGTACGCAGTCCCGGGCGGCCCGGGCGCGGC |
| 34 | 02W643 | 61F | 32 | 119 | CCGCCCGCCGCGCGCCCGCGGATGAGTCCTGAGTAACGCAGCAAAGATTAGACATGGATGAGTT |
| 35 | 02W644 | 61F | 32 | 117 | CCGCCCGCCGCGCGCCCGCGGATGAGTCCTGAGTAACGCCAAAGATTTAGACATGGAGGAGTC |
| 36 | 02W662 | 61F | 32 | rev | CTTAACACGTCCAGACAAGAGGCCCATGTCGACGTAGATCCGTATAGCACTGAGTCGGGAATTGGTACGCAGTCCGCGGGCGCGCGGCGGGCGG |
| 37 | 02W645 | 64F | 33 | 114 | CCCGCGCCGCGGGCGCCGCGGATGAGTCCTGAGTAACGCCTAGTTTGAGCAGTTTTGAGCTGAA |
| 38 | 02W646 | 64F | 33 | 112 | CCCGCGCCGCGGGCGCCGCGGATGAGTCCTGAGTAACGTAGTTTGAGCAGTTTTGAGCTGAG |
| 39 | 02W663 | 64F | 33 | rev | TTAACAAGAAAAATCGGTCAGGACTGTACGCATGCTAACGTTACGGACTATCGGGAATTGGTACGCAGTCCGCGGCGCCCGCGGCGCGGG |
| 40 | 02W647 | 75F | 34 | 109 | GCCGGCGGGCCCGGCCGGCGGATGAGTCCTGAGTAACGCCTTCATATTGATGGTTTTGTTTTGTTA |
| 41 | 02W648 | 75F | 34 | 107 | GCCGGCGGGCCCGGCCGGCGGATGAGTCCTGAGTAACGTTCATATTGATGGTTTTGTTTTTGTTG |
| 42 | 02W664 | 75F | 34 | rev | ACGCTTCTTCCTTGTTGAGAGGGGATGCTCAGGCTATCGACATGGGAATTGGTACGCAGTCCGCCGGCCGGGCCCGCCGGC |
| 43 | 02W649 | 92R | 35 | 104 | CGCCGCCGGGCGCGCGGGCCGATGAGTCCTGAGTAACGCAAGCTTTGCAACAGCAGAAGTGTAT |
| 44 | 02W650 | 92R | 35 | 102 | CGCCGCCGGGCGCGCGGGCCGATGAGTCCTGAGTAACGAGCTTTGCAACAGCAGAAGTGTAC |
| 45 | 02W665 | 92R | 35 | rev | CTCTGCAGAGATAGATCATAACCTTCACGTCATGCTGAGCATGGGAATTGGTACGCAGTCGGCCCGCGCGCCCGGCGGCG |
| 46 | 02W651 | 28R | 36 | 99 | CCGGGCGGGCCGGGCCGCCCGATGAGTCCTGAGTAACGCTCTCTCTTGTTTGTTGCAGGAGCA |
| 47 | 02W652 | 28R | 36 | 97 | CCGGGCGGGCCGGGCCGCCCGATGAGTCCTGAGTAACGCACTCTTGTTTGTTGCAGGAGCT |
| 48 | 02W666 | 28R | 36 | rev | GAACTATAAATTGCTTGCAGGAACCCGCTAACGTTACGGGGAATTGGTACGCAGTCGGGCGGCCCGCCCGCCCGG |

TABLE 3-continued

Oligonucleotide Keylock probes for detection of SNPs from Table 1.

| SEQ ID # | Keylock nr. | Fragment code | Locus nr. | Length (bp) | 5'-PH-3' sequence |
|---|---|---|---|---|---|
| 49 | 02W653 | 14446E10 | 40 | 94 | GCCGGCCGCGGCCCGGCGCGGATGAGTCCTGAGTAACGCGATCACTGGCTGGAACTTCTCCC |
| 50 | 02W654 | 14446E10 | 40 | 92 | GCCGGCCGCGGCCCGGCGCGGATGAGTCCTGAGTAACGATCACTGGCTGGAACTTCTCCG |
| 51 | 02W667 | 14446E10 | 40 | rev | AACTCTCAATTTTTCAACCTTCTCTATCATTCGAGGAATTGGTACGCAGTCCGCGCCGGGCCGCGGCCGC |
| 52 | 02W655 | 14447C06 | 38 | 89 | CCCGCGCGCGGCCGGCCGGCGATGAGTCCTGAGTACGCCATGTATGCATGATTGGCGGTCCA |
| 53 | 02W656 | 14447C06 | 38 | 87 | CCCGCGCGCGGCCGGCCGGCGATGAGTCCTGAGTACGATGTATGCATGATTGGCGGTCCG |
| 54 | 02W668 | 14447C06 | 38 | rev | TTCTTTTGTTATAGCAAGAGCTTGAACGGGGAATGGTACGCAGTCGCCGGCCGGCCGCGCGGG |
| 55 | 02W657 | 14446E01 | 39 | 84 | GGCGCGCGGCCCGCGCGCCGGATGAGTCCTGAGTACGCTGTTGTTCCTTGTTGCATCTCCTTT |
| 56 | 02W658 | 14446E01 | 39 | 82 | GGCGCGCGGCCCGCGCGCCGGATGAGTCCTGAGTACGGTTGTTCCTTGTTGCATCTCCTTG |
| 57 | 02W669 | 14446E01 | 39 | rev | TCACAAGCTCCCATCGCATCATGGGAATTGGTACCAGTCCGGCGCGCGGGCCGCGCGCC |
| 58 | 02W659 | 14157A04 | 37 | 79 | GGCGGCCGCCGGGCGGGCCGGATGAGTGCTGAGTACGTGCAACAGTTGAATAGAAAGATGT |
| 59 | 02W660 | 14157A04 | 37 | 77 | GGCGGCCGCCGGGCGGGCCGGATGAGTCCTGAGTACGCAACAGTTGAATAGAAAGATGC |
| 60 | 02W670 | 14157A04 | 37 | rev | ACACGAGCCTCGGATCAATGGGAATTGGTACGCATCCGGCCCGCCCGGCGGCCGCC |

The invention claimed is:

1. A pair of oligonucleotide probes (K) comprising:
   (a) a first oligonucleotide probe (P1) that comprises
      (i) a first clamp segment (C1), that is capable of hybridizing to a second clamp segment (C2) of a second oligonucleotide probe (P2), and
      (ii) a first target segment (T1) at its 3' end that is capable of hybridizing to a first segment (S1) of a target DNA sequence (D) to be detected;
   (b) a second oligonucleotide probe (P2) that comprises
      (i) a second clamp segment (C2), that is capable of hybridizing to C1, and (ii) a second target segment (T2) at it's 5' end that is capable of hybridizing to a second segment (S2) of D wherein S1 and S2 are located essentially adjacent to one another in D, and wherein the 5' end of S1 is adjacent to the 3' end of S2.

2. A pair of oligonucleotide probes according to claim 1, wherein C1 and C2 when hybridized to each other have a melting temperature $T_{mc}$ which is higher than the melting temperature $T_{mt}$ of each of T1 and T2 when hybridized to a complementary DNA sequence.

3. A pair of oligonucleotide probes according to claim 2, wherein the $T_{mc}$ of hybridized C1 and C2 is at least 1° C. higher than the highest $T_{mt}$ of hybridized T1 and T2.

4. The pair of nucleotide probes of claim 3 wherein the $T_{mc}$ of hybridized C1 and C2 is at least 5° C. higher than the highest $T_{mt}$ of hybridized T1 and T2.

5. The pair of nucleotide probes of claim 4 wherein the $T_{mc}$ of hybridized C1 and C2 is at least 10° C. higher than the highest $T_{mt}$ of T1 and T2.

6. A pair of oligonucleotide probes according to claim 1 wherein the guanylic acid and cytidylic acid (GC) content of C1 and C2 ranges from more than 50% to 100%.

7. A pair of oligonucleotide probes according to claim 6 wherein the GC content of C1 and C2 is >60%.

8. A pair of oligonucleotide probes according to claim 7 wherein the GC content of C1 and C2 is >70%.

9. A pair of oligonucleotide probes according to claim 7 wherein the GC content of C1 and C2 is >80%.

10. A pair of oligonucleotide probes according to claim 7 wherein the GC content of C1 and C2 is between 90% and 100%.

11. A pair of oligonucleotide probes according to claim 1, wherein C1 and C2 comprise, at least one G or C nucleotide more than the number of G or C nucleotides in T1 or T2 of the same length.

12. A pair of oligonucleotide probes according to claim 11 wherein C1 and C2 comprise at least two G or C nucleotides more than the number of G or C nucleotides in T1 or T2 of the same length.

13. A pair of oligonucleotide probes according to claim 12 wherein C1 and C2 comprise at least three G or C nucleotides more than the number of T1 or T2 of the same length.

14. A pair of oligonucleotide probes according to claim 13 wherein C1 and C2 comprise at least four G or C nucleotides more than the number of T1 or T2 of the same length.

15. A pair of oligonucleotide probes according to claim 14 wherein C1 and C2 comprise at least five G or C nucleotides more than the number of T1 or T2 of the same length.

16. A pair of oligonucleotide probes according to claim 1, wherein the C1 and/or C2 comprises modified nucleotides that have an increased binding affinity compared to conventional adenylic acid (A), thymidilic acid (T), cytidylic acid (C) and guanylic acid (G).

17. A pair of oligonucleotide probes according to claim 1, wherein the length of C1 and/or C2 is from 10 to 30 nucleotides.

18. A pair of oligonucleotide probes according to claim 17, wherein the length of T1 and T2 is, independently, 15 to 30 nucleotides.

19. A pair of oligonucleotide probes according to claim 1, wherein P1, P2 or both includes at least one primer binding site designated B1 or B2, respectively.

20. A pair of oligonucleotide probes according to claim 1, wherein P1, and P2 include at least one stuffer sequence designated R1 or R2, respectively.

21. A pair of oligonucleotide probes according to claim 1, wherein the each of T1 and T2 includes at least one allele-specific nucleotide.

22. A pair of oligonucleotide probes according to claim 21, wherein the allele-specific nucleotide is located at the end of T1 or of T2.

23. A set of oligonucleotide probes comprising the pair of oligonucleotides according to claim 21 and at least one additional probe (P3) that includes a target segment T3 having an additional allele specific nucleotide and wherein P3 is distinct from P1 and P2.

24. A pair of oligonucleotides probes according to claim 1, wherein P1 or P2 comprises an additional region that cannot anneal to D, which additional region is located at the end of P1 or P2 at a position that corresponds to a junction site between S1 and S2.

25. A pair of oligonucleotides probes according to claim 24, wherein the additional region creates a cleavable site which site will be cleaved when exposed to a cleaving agent under conditions wherein cleavage can occur.

26. A group of oligonucleotides comprising at least two pairs of probes according to claim 1, wherein the clamp segments C1 and C2 of each pair of probes are designed such that for each probe pair, the combination of C1 and C2 forms a unique combination within the group such that each probe can selectively hybridize to one other probe in the group.

27. A group of oligonucleotides according to claim 26, wherein each C1 and C2 of each pair of probes further includes a unique sequence.

28. A method for the detection of a target nucleotide sequence (D) in a sample comprising the steps of:
 (a) adding to the sample a pair (K) of probes according to claim 1;
 (b) allowing the probes to hybridize to the target sequence;
 (c) ligating T1 and T2 when they are located adjacent to one another when annealed to D to form ligation products; and
 (d) detecting the presence or absence of any ligation products.

29. A method according to claim 28, wherein the ligation products are amplified prior to the detecting step (d).

30. A method according to claim 28, wherein D is amplified prior to hybridization of the probes.

31. A method according to claim 28, wherein the sample includes more than one target nucleotide sequence designated D1 ... Dn, respectively, and wherein a group of more than one pair of oligonucleotide probes designated K1 ... Kn, respectively that correspond to, and are capable of binding to and detecting, D1 ... Dn, respectively, are added to the sample in step (a).

32. A method according to claim 31 wherein the clamp segments C1 and C2 of each pair of probes K1 ... Kn are designed such that for each probe pair K1 ... Kn, the combination of C1 and C2 forms a unique combination within the group such that for each probe pair K1 ... Kn, the probe P1 can selectively hybridize to a unique single probe P2 in the group and not to any other probe P2 in the group.

33. A method according to claim 28 wherein each probe includes a unique sequence.

34. A method according to claim 28 wherein detection is based on measurement or assessment of nucleic acid length, sequence and/or mass.

35. A method according to claim 28 wherein the target sequence D is in a DNA or RNA molecule.

36. A method according to claim 35 wherein the DNA or RNA molecule is in the form of polyA+RNA, cDNA, genomic DNA, organelle DNA, a synthetic nucleic acid, a DNA library, a clone bank or any combination thereof.

37. A set of at least three oligonucleotides suitable for SNP genotyping, comprising:
(a) a first oligonucleotide probe (P1) that comprises
    (i) a first clamp segment (C1) that is capable of hybridizing to a second clamp segment (C2) of a second oligonucleotide probe (P2), and
    (ii) a first target segment (T1) that is capable of hybridizing to a first segment (S1) of a target DNA sequence (D) to be detected;
(b) a second oligonucleotide probe (P2) that comprises
    (i) a second clamp segment (C2) that is capable of hybridizing to C1, and
    (ii) a second target segment (T2) that is capable of hybridizing to a second segment (S2) of D;
(c) at least a third oligonucleotide probe (P3) that comprises C2 and T2;
wherein P2 and P3 include an allele-specific nucleotide, located at the end of T1 or T2 ; and
wherein the allele-specific nucleotide of P2 and P3 corresponds to the alleles of the SNP to be detected; and
wherein P2 and P3 further include a stuffer segment that discriminates between amplified ligation products formed between P1 and P2 or P1 and P3.

38. A kit useful in a method for detecting the presence, absence or amount of a target DNA sequence in a sample, the kit comprising at least one pair of probes as defined in claim 1 and one or more reagents to be used in said detecting method.

39. A kit useful in a method for detecting the presence, absence or amount of a target DNA sequence in a sample, the kit comprising at least one group of probes as defined in claim 26 and one or more reagents to be used in said detecting method.

* * * * *

SEQUENCE LISTING

```
<160> NUMBER OF SEQ ID NOS: 68

<210> SEQ ID NO 1
<211> LENGTH: 472
<212> TYPE: DNA
<213> ORGANISM: Lycopersicon esculentum
<220> FEATURE:
<221> NAME/KEY: misc_feature
<223> OTHER INFORMATION: synthetic oligonucleotide

<400> SEQUENCE: 1
tatccactca ggtctccgca agccagaaat gggatataca ccttgttacg accytcaagc      60
catccactac tgcaatctgt catgtcacag atgttcggaa gataatgtat aagtacaact     120
atatagtcgg awttgcatct agtctagcat tcggaaaatg gaagccatgc tacttctagc     180
ataaaaaaca gcagctagaa atcgtaactc caatgatacg aggaagtatt cagagtttag     240
agtgawgtac aatgcaattt agagaacaag catctgcaca tcraagttac ctaggtcctc     300
agcgcctgat ggacttccaa cttgttcaag aaggcgataa aggtctttct cattgaatcc     360
ttcaggtgga gagtagtttt cacaaactgc aaatgcctct gcacagcgga aagattgaat     420
tagatttatg ttatatagcc attctagtct tgctttaatg gatctttctc ga             472

<210> SEQ ID NO 2
<211> LENGTH: 222
<212> TYPE: DNA
<213> ORGANISM: Lycopersicon esculentum
```

<400> SEQUENCE: 2

```
ccacagtttc atgctgcacc tacatgtgta agcaactatc atagcaagtc tcggaacaat      60
tggtaggaaa aaatcmykta aggatatgaa acatactgty ctttcttcat ctgagtctgy     120
agagttaatt tttaactctt gggataaatg caaagawtta gacatggakg agtycttaac    180
acgtccagac aagaggcgta acacaggtac accttttctc ga                       222
```

<210> SEQ ID NO 3
<211> LENGTH: 133
<212> TYPE: DNA
<213> ORGANISM: Lycopersicon esculentum

<400> SEQUENCE: 3

```
ttgtgcttga tgaattgtag gtccagtgca ggtttgcttc taaaacaggg agcactttgc     60
aagtggtgaa agttctatta gctgggaaag tgtagtttga gcagttttga gctgarttaa   120
caagaaaaat cga                                                        133
```

<210> SEQ ID NO 4
<211> LENGTH: 249
<212> TYPE: DNA
<213> ORGANISM: Lycopersicon esculentum

<400> SEQUENCE: 4

```
ccgccactgg gtaattgagt ttcatattga tggttttgtt tttgttracg cttcttcctt     60
gttgagaggg ttcaatggag agattctatc tcgtcctcca ttagttgaag ctattgcctt   120
tgatcctatc ctttcaaagg ycaagatgat tgcagataat tggaatccat taaccaatga   180
ttctacggaa aatttattcc ctcactggag gagatgggca gagataaata tgagattttg   240
tgatgacat                                                             249
```

<210> SEQ ID NO 5
<211> LENGTH: 284
<212> TYPE: DNA
<213> ORGANISM: Lycopersicon esculentum

<400> SEQUENCE: 5

```
tcgagtaagg cggatggata tggaacaagc catttcaagg agcaatttcc caggattttc     60
agctttgcaa cagcagaagt gtayctctgc agagatagat cataaccttt ggaaaggtgt   120
agtaattgtc aaagggagga atgagccagg aaactgatag actatgttgc gaaaataagc   180
tatacttcac taaaaaaagg ctagacgttt gagaaatgaa gcaagaacta acacctctca   240
ccaattgcat cattttctta gttcagttga tgtgatgagc ttgt                    284
```

<210> SEQ ID NO 6
<211> LENGTH: 320
<212> TYPE: DNA
<213> ORGANISM: Lycopersicon esculentum

<400> SEQUENCE: 6

```
tcgatatccw ctcttgtttg ttgcaggagc wgaactataa attgcttgca ggaaccttga     60
catatgcttt ctgttgagac ttgaatcacc agcatggatt tgaatgcctt gcccacagcca   120
gaggatgacg aygagatttt tggacaacaa ttagaagatg aaccacaaga acctatttta   180
cgtagtgatg agcstgcaga ttatgtcacg agtgctgtag agatttcacg tcgcgtatgt   240
ttctgcttat actgctcgct gtatcaacta ttgaacygta ctactacttg arcttgctcg   300
```
tttattggat atttcttttt                                              320

<210> SEQ ID NO 7
<211> LENGTH: 191
<212> TYPE: DNA
<213> ORGANISM: Lycopersicon esculentum

<400> SEQUENCE: 7
gaattcacac tasgttcgat gaaattgaaa cgttctcttt ctgaagaaka tacacaagaa    60
aaaatcttat agtcctcaac aatattcttc ttcgtaacag aaaacacgga agaaaatctc   120
ttctgaaaat ccctataatc actggctgga acttctccsa actctcaatt tttcaacctt   180
ctctatgtta a                                                       191

<210> SEQ ID NO 8
<211> LENGTH: 279
<212> TYPE: DNA
<213> ORGANISM: Lycopersicon esculentum

<400> SEQUENCE: 8
ctgcagaadt actgtttgtt caggacttac taaatatcct aaacaaaatt gatgatagag    60
ccaataatgt atgcatgatt ggcggtccrt tcttttgtta tagcaagagc ttgaagctaa   120
ttttgtttgt cataatggcc gcactaattg tttattatct cagaatgaac aaaaagaagc   180
aagtcagaag cttttstactc tatactgaac aactttggaa ttggaactat gtacttatct   240
agccacgcct catagatctt tgtggtttag gagtgttaa                          279

<210> SEQ ID NO 9
<211> LENGTH: 336
<212> TYPE: DNA
<213> ORGANISM: Lycopersicon esculentum

<400> SEQUENCE: 9
gaattcacaa tgaaaaakgk dgtaaaaaca cgaaatcaat caagcatgca agagataatg    60
ttgtccatcc agttgttgtt gatgtttcgg tattgtatgt gtgttgggag gagttatctg   120
grcagcaagt cgaggtttga acgtcaaaaa ggtatgggtt gtcttctctc tttgtccctt   180
ttcgaagaga ccccctaaggt tcagacgaat ctattccaaa aactagggtt gttccttgtt   240
gcatctcctt ktcacaagct cccatcgcat cataagtagg gtatgtttga tggtagaatt   300
tacggatgta atttactttt gaaatgatta tgttaa                             336

<210> SEQ ID NO 10
<211> LENGTH: 373
<212> TYPE: DNA
<213> ORGANISM: Lycopersicon esculentum

<400> SEQUENCE: 10
agagagacga gagctcgact agtgatagtg ttatgtgcaa cagttgaata gaaagatgya    60
cacgagcctc ggatcaatgg cagggaaaga ggcgtggtgc tacgaaccat aaaggcaagg   120
ttgagctttc ctttacagag tacatcgcct attccatact ccgctgatac tctttgataa   180
atcaaaatct gtggtgatct cgtagttctt ggggatccca gccaaaacca ccttcgaggt   240
tcaacacaac atagacagta tggcagaata tcaagacaat gactgctcga aactgctgat   300
ggcattatgt gcaaccgttg aatagagaga tgtacacgag tctcggatca atggcaggaa   360
aagagagtgc ttg                                                     373

```
<210> SEQ ID NO 11
<211> LENGTH: 124
<212> TYPE: DNA
<213> ORGANISM: Artificial
<220> FEATURE:
<221> NAME/KEY: misc_feature
<223> OTHER INFORMATION: oligonucleotide

<400> SEQUENCE: 11
gtacaatgca atttagagaa caagcgggaa ttggtacgca gtcgatgagt cctgagtaac      60
gctgatccga tcgatatcga cgtagctgca tcgtaatcgg gaagtattca gagtttagag     120
tgaa                                                                  124

<210> SEQ ID NO 12
<211> LENGTH: 122
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 12
gtacaatgca atttagagaa caagcgggaa ttggtacgca gtcgatgagt cctgagtaac      60
gcatccgatc gatatcgacg tagctgcatc gtaatcggga agtattcaga gtttagagtg     120
at                                                                    122

<210> SEQ ID NO 13
<211> LENGTH: 119
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 13
cttaacacgt ccagacaaga ggcgggaatt ggtacgcagt cgatgagtcc tgagtaacgc      60
accatgtcga cgtagatccg tatagcactg agtcgcaaag aattagacat ggatgagtt      119

<210> SEQ ID NO 14
<211> LENGTH: 117
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 14
cttaacacgt ccagacaaga ggcgggaatt ggtacgcagt cgatgagtcc tgagtaacgc      60
ccatgtcgac gtagatccgt atagcactga gtccaaagat ttagacatgg aggagtc        117

<210> SEQ ID NO 15
<211> LENGTH: 114
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 15
ttaacaagaa aaatcggtca ggactgggaa ttggtacgca gtcgatgagt cctgagtaac      60
gccgtacgca tgctaacgtt acggactatc tagtttgagc agttttgagc tgaa           114
```

```
<210> SEQ ID NO 16
<211> LENGTH: 112
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 16
ttaacaagaa aaatcggtca ggactgggaa ttggtacgca gtcgatgagt cctgagtaac      60
gctacgcatg ctaacgttac ggactatcta gtttgagcag ttttgagctg ag            112

<210> SEQ ID NO 17
<211> LENGTH: 109
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 17
acgcttcttc cttgttgaga gggggaatt ggtacgcagt cgatgagtcc tgagtaacgc       60
cgatgctcag gctatcgaca tgttcatatt gatggttttg tttttgtta              109

<210> SEQ ID NO 18
<211> LENGTH: 107
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 18
acgcttcttc cttgttgaga gggggaatt ggtacgcagt cgatgagtcc tgagtaacgc       60
atgctcaggc tatcgacatg ttcatattga tggttttgtt tttgttg               107

<210> SEQ ID NO 19
<211> LENGTH: 104
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 19
ctctgcagag atagatcata acctgggaat tggtacgcag tcgatgagtc ctgagtaacg      60
catcacgtca tgctgagcat agctttgcaa cagcagaagt gtat                  104

<210> SEQ ID NO 20
<211> LENGTH: 102
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 20
ctctgcagag atagatcata acctgggaat tggtacgcag tcgatgagtc ctgagtaacg      60
ccacgtcatg ctgagcatag ctttgcaaca gcagaagtgt ac                    102

<210> SEQ ID NO 21
<211> LENGTH: 99
<212> TYPE: DNA
<213> ORGANISM: Artificial
```

<220> FEATURE:
<221> NAME/KEY: misc_feature
<223> OTHER INFORMATION: synthetic oligonucleotide

<400> SEQUENCE: 21
gaactataaa ttgcttgcag gaaccgggaa ttggtacgca gtcgatgagt cctgagtaac    60
gctcgctaac gttacgctct cttgtttgtt gcaggagca                          99

<210> SEQ ID NO 22
<211> LENGTH: 97
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 22
gaactataaa ttgcttgcag gaaccgggaa ttggtacgca gtcgatgagt cctgagtaac    60
gcgctaacgt tacgcactct tgtttgttgc aggagct                            97

<210> SEQ ID NO 23
<211> LENGTH: 94
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 23
aactctcaat ttttcaacct tctctaggga attggtacgc agtcgatgag tcctgagtaa    60
cgcgtcattc gaatcactgg ctggaacttc tccc                               94

<210> SEQ ID NO 24
<211> LENGTH: 92
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 24
aactctcaat ttttcaacct tctctaggga attggtacgc agtcgatgag tcctgagtaa    60
cgccattcga atcactggct ggaacttctc cg                                 92

<210> SEQ ID NO 25
<211> LENGTH: 89
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 25
ttcttttgtt atagcaagag cttgaaggga attggtacgc agtcgatgag tcctgagtaa    60
cgcccgatgt atgcatgatt ggcggtcca                                     89

<210> SEQ ID NO 26
<211> LENGTH: 87
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 26
ttcttttgtt atagcaagag cttgaaggga attggtacgc agtcgatgag tcctgagtaa      60
cgccatgtat gcatgattgg cggtccg                                          87

<210> SEQ ID NO 27
<211> LENGTH: 84
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 27
tcacaagctc ccatcgcatc atgggaattg gtacgcagtc gatgagtcct gagtaacgct      60
gttgttcctt gttgcatctc cttt                                             84

<210> SEQ ID NO 28
<211> LENGTH: 82
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 28
tcacaagctc ccatcgcatc atgggaattg gtacgcagtc gatgagtcct gagtaacggt      60
tgttccttgt tgcatctcct tg                                               82

<210> SEQ ID NO 29
<211> LENGTH: 79
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 29
acacgagcct cggatcaatg ggaattggta cgcagtcgat gagtcctgag taacgtgcaa      60
cagttgaata gaaagatgt                                                   79

<210> SEQ ID NO 30
<211> LENGTH: 77
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 30
acacgagcct cggatcaatg ggaattggta cgcagtcgat gagtcctgag taacgcaaca      60
gttgaataga aagatgc                                                     77

<210> SEQ ID NO 31
<211> LENGTH: 65
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 31
gccgcgcccg ggccgcccgg gatgagtcct gagtaacgct ggaagtattc agagtttaga      60

```
gtgaa                                                               65

<210> SEQ ID NO 32
<211> LENGTH: 63
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 32
gccgcgcccg ggccgcccgg gatgagtcct gagtaacggg aagtattcag agtttagagt    60
gat                                                                 63

<210> SEQ ID NO 33
<211> LENGTH: 99
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 33
gtacaatgca atttagagaa caagcgatcc gatcgatatc gacgtagctg catcgtaatc    60
ggggaattgg tacgcagtcc cgggcggccc gggcgcggc                          99

<210> SEQ ID NO 34
<211> LENGTH: 65
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 34
ccgcccgccg cgcgcccgcg gatgagtcct gagtaacgca gcaaagaatt agacatggat    60
gagtt                                                               65

<210> SEQ ID NO 35
<211> LENGTH: 63
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 35
ccgcccgccg cgcgcccgcg gatgagtcct gagtaacgcc aaagatttag acatggagga    60
gtc                                                                 63

<210> SEQ ID NO 36
<211> LENGTH: 94
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 36
cttaacacgt ccagacaaga ggcccatgtc gacgtagatc cgtatagcac tgagtcggga    60
attggtacgc agtccgcggg cgcgcggcgg gcgg                               94

<210> SEQ ID NO 37
```

```
<211> LENGTH: 64
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 37
cccgcgccgc gggcgccgcg gatgagtcct gagtaacgcc tagtttgagc agttttgagc    60
tgaa                                                                 64

<210> SEQ ID NO 38
<211> LENGTH: 62
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 38
cccgcgccgc gggcgccgcg gatgagtcct gagtaacgta gtttgagcag ttttgagctg    60
ag                                                                   62

<210> SEQ ID NO 39
<211> LENGTH: 90
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 39
ttaacaagaa aaatcggtca ggactgtacg catgctaacg ttacggacta tcgggaattg    60
gtacgcagtc cgcggcgccc gcggcgcggg                                     90

<210> SEQ ID NO 40
<211> LENGTH: 67
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 40
gccggcgggc ccggccggcg gatgagtcct gagtaacgcc ttcatattga tggttttgtt    60
tttgtta                                                              67

<210> SEQ ID NO 41
<211> LENGTH: 65
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 41
gccggcgggc ccggccggcg gatgagtcct gagtaacgtt catattgatg gttttgtttt    60
tgttg                                                                65

<210> SEQ ID NO 42
<211> LENGTH: 82
<212> TYPE: DNA
<213> ORGANISM: Artificial
<220> FEATURE:
```

<221> NAME/KEY: misc_feature
<223> OTHER INFORMATION: synthetic oligonucleotide

<400> SEQUENCE: 42
acgcttcttc cttgttgaga ggggatgctc aggctatcga catgggaat tggtacgcag    60 tccgccggcc gggcccgccg gc    82

<210> SEQ ID NO 43
<211> LENGTH: 64
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 43
cgccgccggg cgcgcgggcc gatgagtcct gagtaacgca agctttgcaa cagcagaagt    60
gtat    64

<210> SEQ ID NO 44
<211> LENGTH: 62
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 44
cgccgccggg cgcgcgggcc gatgagtcct gagtaacgag ctttgcaaca gcagaagtgt    60
ac    62

<210> SEQ ID NO 45
<211> LENGTH: 80
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 45
ctctgcagag atagatcata accttcacgt catgctgagc atgggaattg gtacgcagtc    60
ggcccgcgcg cccggcggcg    80

<210> SEQ ID NO 46
<211> LENGTH: 63
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 46
ccgggcgggc cgggccgccc gatgagtcct gagtaacgct ctctcttgtt tgttgcagga    60
gca    63

<210> SEQ ID NO 47
<211> LENGTH: 61
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 47

```
ccgggcgggc cgggccgccc gatgagtcct gagtaacgca ctcttgtttg ttgcaggagc    60
t                                                                    61

<210> SEQ ID NO 48
<211> LENGTH: 76
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 48
gaactataaa ttgcttgcag gaacccgcta acgttacggg gaattggtac gcagtcgggc    60
ggcccggccc gcccgg                                                    76

<210> SEQ ID NO 49
<211> LENGTH: 62
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 49
gccggccgcg gcccggcgcg gatgagtcct gagtaacgcg atcactggct ggaacttctc    60
cc                                                                   62

<210> SEQ ID NO 50
<211> LENGTH: 60
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 50
gccggccgcg gcccggcgcg gatgagtcct gagtaacgat cactggctgg aacttctccg    60

<210> SEQ ID NO 51
<211> LENGTH: 72
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 51
aactctcaat ttttcaacct tctctatcat tcgagggaat tggtacgcag tccgcgccgg    60
gccgcggccg gc                                                        72

<210> SEQ ID NO 52
<211> LENGTH: 63
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 52
cccgcgcgcg gccggccggc gatgagtcct gagtaacgcc atgtatgcat gattggcggt    60
cca                                                                  63
```

```
<210> SEQ ID NO 53
<211> LENGTH: 61
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 53
cccgcgcgcg gccggccggc gatgagtcct gagtaacgat gtatgcatga ttggcggtcc      60
g                                                                     61

<210> SEQ ID NO 54
<211> LENGTH: 66
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 54 ttctttgtt atagcaagag cttgaacggg gaattggtac gcagtcgccg gccggccgcg       60
cgcggg                                                                66

<210> SEQ ID NO 55
<211> LENGTH: 64
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 55
ggcgcgcggc ccgcgcgccg gatgagtcct gagtaacgct gttgttcctt gttgcatctc      60
cttt                                                                  64

<210> SEQ ID NO 56
<211> LENGTH: 62
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 56
ggcgcgcggc ccgcgcgccg gatgagtcct gagtaacggt tgttccttgt tgcatctcct      60
tg                                                                    62

<210> SEQ ID NO 57
<211> LENGTH: 60
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 57
tcacaagctc ccatcgcatc atgggaattg gtacgcagtc cggcgcgcgg gccgcgcgcc      60

<210> SEQ ID NO 58
<211> LENGTH: 62
<212> TYPE: DNA
<213> ORGANISM: Artificial
<220> FEATURE:
<221> NAME/KEY: misc_feature
```

-continued

<223> OTHER INFORMATION: synthetic oligonucleotide

<400> SEQUENCE: 58
ggcggccgcc gggcgggccg gatgagtcct gagtaacgtg caacagttga atagaaagat    60
gt                                                                  62

<210> SEQ ID NO 59
<211> LENGTH: 60
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 59
ggcggccgcc gggcgggccg gatgagtcct gagtaacgca acagttgaat agaaagatgc    60

<210> SEQ ID NO 60
<211> LENGTH: 57
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 60
acacgagcct cggatcaatg ggaattggta cgcagtccgg cccgcccggc ggccgcc       57

<210> SEQ ID NO 61
<211> LENGTH: 16
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 61
gatgagtcct gagtaa                                                   16

<210> SEQ ID NO 62
<211> LENGTH: 16
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 62
gactgcgtac caattc                                                   16

<210> SEQ ID NO 63
<211> LENGTH: 67
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 63
gccggcgggc cggccggcg gatgagtcct gagtaacgcc ttcatattga tggttttgtt    60
tttgtta                                                             67

<210> SEQ ID NO 64
<211> LENGTH: 65
<212> TYPE: DNA

```
<213> ORGANISM: Artificial
<220> FEATURE:
<221> NAME/KEY: misc_feature
<223> OTHER INFORMATION: synthetic oligonucleotide

<400> SEQUENCE: 64
gccggcgggc ccggccggcg gatgagtcct gagtaacgtt catattgatg gttttgtttt      60
tgttg                                                                 65

<210> SEQ ID NO 65
<211> LENGTH: 64
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 65
ggcgcgcggc ccgcgcgccg gatgagtcct gagtaacgct gttgttcctt gttgcatctc      60
cttt                                                                  64

<210> SEQ ID NO 66
<211> LENGTH: 62
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 66
ggcgcgcggc ccgcgcgccg gatgagtcct gagtaacggt tgttccttgt tgcatctcct      60
tg                                                                    62

<210> SEQ ID NO 67
<211> LENGTH: 82
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 67
acgcttcttc cttgttgaga ggggatgctc aggctatcga catggggaat tggtacgcag      60
tccgccggcc gggcccgccg gc                                              82

<210> SEQ ID NO 68
<211> LENGTH: 60
<212> TYPE: DNA
<213> ORGANISM: Artificial
<220> FEATURE:
<221> NAME/KEY: misc_feature
<223> OTHER INFORMATION: synthetic oligonucleotide

<400> SEQUENCE: 68
tcacaagctc ccatcgcatc atgggaattg gtacgcagtc cggcgcgcgg gccgcgcgcc      60
```